US012755414B2

(12) United States Patent
Montgomery et al.

(10) Patent No.: US 12,755,414 B2
(45) Date of Patent: Oct. 6, 2026

(54) TOUCHLESS VOLUME WAVEFORM SAMPLING TO DETERMINE RESPIRATION RATE

(71) Applicant: Covidien LP, Mansfield, MA (US)

(72) Inventors: Dean Montgomery, Edinburgh (GB); Andre Antunes, Edinburgh (GB); Paul S. Addison, Edinburgh (GB)

(73) Assignee: Covidien LP, Mansfield, MA (US)

( * ) Notice: Subject to any disclaimer, the term of this patent is extended or adjusted under 35 U.S.C. 154(b) by 402 days.

(21) Appl. No.: 18/484,273

(22) Filed: Oct. 10, 2023

(65) Prior Publication Data

US 2024/0127469 A1 Apr. 18, 2024

Related U.S. Application Data

(60) Provisional application No. 63/379,541, filed on Oct. 14, 2022.

(51) Int. Cl.
*G06T 7/62* (2017.01)
*A61B 5/08* (2006.01)
(Continued)

(52) U.S. Cl.
CPC .............. *G06T 7/62* (2017.01); *A61B 5/0816* (2013.01); *G06T 7/11* (2017.01); *G06T 7/248* (2017.01);
(Continued)

(58) Field of Classification Search
CPC ......... A61B 5/0816; G06T 7/11; G06T 7/248; G06T 7/55; G06T 7/62; G06T 7/73; G06T 2207/10016; G06T 2207/30196
See application file for complete search history.

(56) References Cited

U.S. PATENT DOCUMENTS 5,107,845 A 4/1992 Guern et al.
5,408,998 A 4/1995 Mersch
(Continued)

FOREIGN PATENT DOCUMENTS

CA 2234191 A1 10/1998
CN 106725410 A 5/2017
(Continued)

OTHER PUBLICATIONS

Massaroni et al. "Non-contact monitoring of breathing pattern and respiratory rate via RGB signal measurement." Sensors 19.12 (2019): 2758. (Year: 2019).*
(Continued)

*Primary Examiner* — Katrina R Fujita
(74) *Attorney, Agent, or Firm* — Dymera IP, LLC

(57) ABSTRACT

An example system includes a camera system, memory, and processing circuitry coupled to the camera system and memory. The processing circuitry is configured to obtain image data and determine a visualization mask based on pixels associated with respiration. The processing circuitry is configured to determine a bounding box based on the visualization mask. The processing circuitry is configured to determine a sampling region for the image data based on an average including the bounding box and at least one previously determined bounding box. The processing circuitry is configured to determine at least a portion of a volume waveform based at least in part on the sampling region, determine at least one respiration parameter based on the volume waveform, and output, for display, the at least one respiration parameter.

13 Claims, 9 Drawing Sheets

(51) Int. Cl.
*G06T 7/11* (2017.01)
*G06T 7/246* (2017.01)
*G06T 7/55* (2017.01)
*G06T 7/73* (2017.01)

(52) U.S. Cl.
CPC .................. *G06T 7/55* (2017.01); *G06T 7/73* (2017.01); *G06T 2207/10016* (2013.01); *G06T 2207/30196* (2013.01)

(56) References Cited

U.S. PATENT DOCUMENTS

| | | | |
|---|---|---|---|
| 5,704,367 | A | 1/1998 | Ishikawa et al. |
| 5,800,360 | A | 9/1998 | Kisner et al. |
| 5,995,856 | A | 11/1999 | Mannheimer et al. |
| 6,241,684 | B1 | 6/2001 | Amano et al. |
| 6,668,071 | B1 | 12/2003 | Minkin et al. |
| 6,920,236 | B2 | 7/2005 | Prokoski |
| 7,431,700 | B2 | 10/2008 | Aoki et al. |
| 7,558,618 | B1 | 7/2009 | Williams |
| 8,149,273 | B2 | 4/2012 | Liu et al. |
| 8,754,772 | B2 | 6/2014 | Horng et al. |
| 8,792,969 | B2 | 7/2014 | Bernal et al. |
| 8,971,985 | B2 | 3/2015 | Bernal et al. |
| 9,226,691 | B2 | 1/2016 | Bernal et al. |
| 9,282,725 | B2 | 3/2016 | Jensen-Jarolim et al. |
| 9,301,710 | B2 | 4/2016 | Mestha et al. |
| 9,402,601 | B1 | 8/2016 | Berger et al. |
| 9,436,984 | B2 | 9/2016 | Xu et al. |
| 9,443,289 | B2 | 9/2016 | Xu et al. |
| 9,504,426 | B2 | 11/2016 | Kyal et al. |
| 9,508,141 | B2 | 11/2016 | Khachaturian et al. |
| 9,607,138 | B1 | 3/2017 | Baldwin et al. |
| 9,662,022 | B2 | 5/2017 | Kyal et al. |
| 9,693,693 | B2 | 7/2017 | Farag et al. |
| 9,693,710 | B2 | 7/2017 | Mestha et al. |
| 9,697,599 | B2 | 7/2017 | Prasad et al. |
| 9,750,461 | B1 | 9/2017 | Telfort |
| 9,839,756 | B2 | 12/2017 | Klasek |
| 9,943,371 | B2 | 4/2018 | Bresch et al. |
| 10,213,540 | B2 | 2/2019 | Burbank et al. |
| 10,278,585 | B2 | 5/2019 | Ferguson et al. |
| 10,376,147 | B2 | 8/2019 | Wood et al. |
| 10,398,353 | B2 | 9/2019 | Addison et al. |
| 10,447,972 | B2 | 10/2019 | Patil |
| 10,489,912 | B1 | 11/2019 | Brailovskiy |
| 10,523,852 | B2 | 12/2019 | Tzvieli et al. |
| 10,588,779 | B2 | 3/2020 | Vorhees et al. |
| 10,589,916 | B2 | 3/2020 | Mcrae |
| 10,650,585 | B2 | 5/2020 | Kiely |
| 10,667,723 | B2 | 6/2020 | Jacquel et al. |
| 10,702,188 | B2 | 7/2020 | Addison et al. |
| 10,729,357 | B2 | 8/2020 | Larson et al. |
| 10,874,331 | B2 | 12/2020 | Kaiser et al. |
| 10,937,296 | B1 | 3/2021 | Kukreja et al. |
| 10,939,824 | B2 | 3/2021 | Addison et al. |
| 10,939,834 | B2 | 3/2021 | Khwaja et al. |
| 10,966,059 | B1 | 3/2021 | Dayal et al. |
| 11,311,252 | B2 | 4/2022 | Jacquel et al. |
| 11,315,275 | B2 | 4/2022 | Addison et al. |
| 11,317,828 | B2 | 5/2022 | Addison et al. |
| 11,350,850 | B2 | 6/2022 | Jacquel et al. |
| 11,850,026 | B2 | 12/2023 | Levi et al. |
| 2002/0137464 | A1 | 9/2002 | Dolgonos et al. |
| 2004/0001633 | A1 | 1/2004 | Caviedes |
| 2004/0258285 | A1 | 12/2004 | Hansen et al. |
| 2005/0203348 | A1 | 9/2005 | Shihadeh et al. |
| 2007/0116328 | A1 | 5/2007 | Sablak et al. |
| 2008/0001735 | A1 | 1/2008 | Tran |
| 2008/0108880 | A1 | 5/2008 | Young et al. |
| 2008/0279420 | A1 | 11/2008 | Masticola et al. |
| 2008/0295837 | A1 | 12/2008 | McCormick et al. |
| 2009/0024012 | A1 | 1/2009 | Li et al. |
| 2009/0141124 | A1 | 6/2009 | Liu et al. |
| 2009/0304280 | A1 | 12/2009 | Aharoni et al. |
| 2010/0210924 | A1 | 8/2010 | Parthasarathy et al. |
| 2010/0236553 | A1 | 9/2010 | Jafari et al. |
| 2010/0249630 | A1 | 9/2010 | Droitcour et al. |
| 2010/0324437 | A1 | 12/2010 | Freeman et al. |
| 2011/0144517 | A1 | 6/2011 | Cervantes |
| 2011/0150274 | A1 | 6/2011 | Patwardhan et al. |
| 2012/0065533 | A1 | 3/2012 | Carrillo et al. |
| 2012/0075464 | A1 | 3/2012 | Derenne et al. |
| 2012/0195473 | A1 | 8/2012 | De Haan et al. |
| 2012/0243797 | A1 | 9/2012 | Di Venuto Dayer et al. |
| 2013/0073312 | A1 | 3/2013 | Thompson et al. |
| 2013/0267873 | A1 | 10/2013 | Fuchs |
| 2013/0271591 | A1 | 10/2013 | Van Leest et al. |
| 2013/0272393 | A1 | 10/2013 | Kirenko et al. |
| 2013/0275873 | A1 | 10/2013 | Shaw et al. |
| 2013/0324830 | A1 | 12/2013 | Bernal et al. |
| 2013/0324876 | A1 | 12/2013 | Bernal et al. |
| 2014/0023235 | A1 | 1/2014 | Cennini et al. |
| 2014/0052006 | A1 | 2/2014 | Lee et al. |
| 2014/0053840 | A1 | 2/2014 | Liu |
| 2014/0073860 | A1 | 3/2014 | Urtti |
| 2014/0139405 | A1 | 5/2014 | Ribble et al. |
| 2014/0140592 | A1 | 5/2014 | Lasenby et al. |
| 2014/0235976 | A1 | 8/2014 | Bresch et al. |
| 2014/0267718 | A1 | 9/2014 | Govro et al. |
| 2014/0272860 | A1 | 9/2014 | Peterson et al. |
| 2014/0275832 | A1 | 9/2014 | Muehlsteff et al. |
| 2014/0276104 | A1 | 9/2014 | Tao et al. |
| 2014/0330336 | A1 | 11/2014 | Errico et al. |
| 2014/0334697 | A1 | 11/2014 | Kersten et al. |
| 2014/0358017 | A1 | 12/2014 | Op Den Buijs et al. |
| 2014/0378810 | A1 | 12/2014 | Davis et al. |
| 2014/0379369 | A1 | 12/2014 | Kokovidis et al. |
| 2015/0003723 | A1 | 1/2015 | Huang et al. |
| 2015/0068069 | A1 | 3/2015 | Tran et al. |
| 2015/0094597 | A1 | 4/2015 | Mestha et al. |
| 2015/0131880 | A1 | 5/2015 | Wang et al. |
| 2015/0157269 | A1 | 6/2015 | Lisogurski et al. |
| 2015/0198707 | A1 | 7/2015 | Al-Alusi |
| 2015/0223731 | A1 | 8/2015 | Sahin |
| 2015/0238150 | A1 | 8/2015 | Subramaniam |
| 2015/0265187 | A1 | 9/2015 | Bernal et al. |
| 2015/0282724 | A1 | 10/2015 | Mcduff et al. |
| 2015/0286779 | A1 | 10/2015 | Bala et al. |
| 2015/0301590 | A1 | 10/2015 | Furst et al. |
| 2015/0317814 | A1 | 11/2015 | Johnston et al. |
| 2015/0379370 | A1 | 12/2015 | Clifton et al. |
| 2016/0000335 | A1 | 1/2016 | Khachaturian et al. |
| 2016/0049094 | A1 | 2/2016 | Gupta et al. |
| 2016/0082222 | A1 | 3/2016 | Garcia Molina et al. |
| 2016/0140828 | A1 | 5/2016 | Deforest |
| 2016/0143598 | A1 | 5/2016 | Rusin et al. |
| 2016/0151022 | A1 | 6/2016 | Berlin et al. |
| 2016/0156835 | A1 | 6/2016 | Ogasawara et al. |
| 2016/0174887 | A1 | 6/2016 | Kirenko et al. |
| 2016/0210747 | A1 | 7/2016 | Hay et al. |
| 2016/0235344 | A1 | 8/2016 | Auerbach |
| 2016/0310084 | A1 | 10/2016 | Banerjee et al. |
| 2016/0317041 | A1 | 11/2016 | Porges et al. |
| 2016/0345931 | A1 | 12/2016 | Xu et al. |
| 2016/0367186 | A1 | 12/2016 | Freeman et al. |
| 2017/0007342 | A1 | 1/2017 | Kasai et al. |
| 2017/0007795 | A1 | 1/2017 | Pedro et al. |
| 2017/0055877 | A1 | 3/2017 | Niemeyer |
| 2017/0065484 | A1 | 3/2017 | Addison et al. |
| 2017/0071516 | A1 | 3/2017 | Bhagat et al. |
| 2017/0095215 | A1 | 4/2017 | Watson et al. |
| 2017/0095217 | A1 | 4/2017 | Hubert et al. |
| 2017/0119340 | A1 | 5/2017 | Nakai et al. |
| 2017/0147772 | A1 | 5/2017 | Meehan et al. |
| 2017/0164904 | A1 | 6/2017 | Kirenko |
| 2017/0172434 | A1 | 6/2017 | Amelard et al. |
| 2017/0173262 | A1 | 6/2017 | Veltz |
| 2017/0238805 | A1 | 8/2017 | Addison et al. |
| 2017/0238842 | A1 | 8/2017 | Jacquel et al. |
| 2017/0311887 | A1 | 11/2017 | Leussler et al. |
| 2017/0319114 | A1 | 11/2017 | Kaestle |
| 2018/0042486 | A1 | 2/2018 | Yoshizawa et al. |
| 2018/0042500 | A1 | 2/2018 | Liao et al. |

(56) References Cited

U.S. PATENT DOCUMENTS

| | | | |
|---|---|---|---|
| 2018/0049669 A1 | 2/2018 | Vu et al. | |
| 2018/0053392 A1 | 2/2018 | White et al. | |
| 2018/0104426 A1 | 4/2018 | Oldfield et al. | |
| 2018/0106897 A1 | 4/2018 | Shouldice et al. | |
| 2018/0169361 A1 | 6/2018 | Dennis et al. | |
| 2018/0217660 A1 | 8/2018 | Dayal et al. | |
| 2018/0228381 A1 | 8/2018 | Leboeuf et al. | |
| 2018/0303351 A1 | 10/2018 | Mestha et al. | |
| 2018/0310844 A1 | 11/2018 | Tezuka et al. | |
| 2018/0325420 A1 | 11/2018 | Gigi | |
| 2018/0333050 A1 | 11/2018 | Greiner et al. | |
| 2018/0333102 A1 | 11/2018 | De Haan et al. | |
| 2018/0352150 A1 | 12/2018 | Purwar et al. | |
| 2019/0050985 A1 | 2/2019 | Den Brinker et al. | |
| 2019/0130191 A1* | 5/2019 | Zhou | G06V 20/52 |
| 2019/0133499 A1 | 5/2019 | Auerbach | |
| 2019/0142274 A1 | 5/2019 | Addison et al. | |
| 2019/0199970 A1 | 6/2019 | Greiner et al. | |
| 2019/0209046 A1 | 7/2019 | Addison et al. | |
| 2019/0209083 A1 | 7/2019 | Wu et al. | |
| 2019/0307365 A1 | 10/2019 | Addison et al. | |
| 2019/0311101 A1 | 10/2019 | Nienhouse | |
| 2019/0343480 A1 | 11/2019 | Shute et al. | |
| 2019/0380599 A1 | 12/2019 | Addison et al. | |
| 2019/0380807 A1 | 12/2019 | Addison et al. | |
| 2020/0046302 A1 | 2/2020 | Jacquel et al. | |
| 2020/0187827 A1 | 6/2020 | Addison et al. | |
| 2020/0202154 A1 | 6/2020 | Wang et al. | |
| 2020/0205734 A1 | 7/2020 | Mulligan et al. | |
| 2020/0237225 A1 | 7/2020 | Addison et al. | |
| 2020/0242790 A1 | 7/2020 | Addison et al. | |
| 2020/0250406 A1 | 8/2020 | Wang et al. | |
| 2020/0253560 A1 | 8/2020 | De Haan | |
| 2020/0279464 A1 | 9/2020 | Llewelyn | |
| 2020/0289024 A1 | 9/2020 | Addison et al. | |
| 2020/0294257 A1* | 9/2020 | Yoo | G06N 3/084 |
| 2020/0329976 A1 | 10/2020 | Chen et al. | |
| 2020/0409383 A1 | 12/2020 | Maunder | |
| 2021/0056663 A1* | 2/2021 | Zhang | G06T 11/60 |
| 2021/0068670 A1 | 3/2021 | Redtel | |
| 2021/0142874 A1 | 5/2021 | Llewelyn | |
| 2021/0153746 A1 | 5/2021 | Addison et al. | |
| 2021/0201517 A1 | 7/2021 | Yang et al. | |
| 2021/0233631 A1 | 7/2021 | Llewelyn | |
| 2021/0235992 A1 | 8/2021 | Addison | |
| 2021/0295662 A1 | 9/2021 | Bugbee et al. | |
| 2021/0313075 A1 | 10/2021 | Mc Namara et al. | |
| 2021/0365707 A1* | 11/2021 | Mao | G06V 10/62 |
| 2022/0211296 A1 | 7/2022 | Addison et al. | |
| 2022/0233096 A1* | 7/2022 | Smit | A61B 5/091 |
| 2023/0122367 A1 | 4/2023 | Tesar | |

FOREIGN PATENT DOCUMENTS

| | | | |
|---|---|---|---|
| CN | 111728602 | A | 10/2020 |
| CN | 112233813 | A | 1/2021 |
| DE | 19741982 | A1 | 10/1998 |
| EP | 2793189 | B1 | 11/2016 |
| EP | 2428162 | B1 | 8/2017 |
| EP | 3207862 | A1 | 8/2017 |
| EP | 3207863 | A1 | 8/2017 |
| EP | 3384827 | A1 | 10/2018 |
| EP | 2772828 | B1 | 1/2019 |
| JP | 2004173010 | A | 6/2004 |
| JP | 2004283373 | A | 10/2004 |
| JP | 3744778 | B2 | 12/2005 |
| JP | 2009544080 | A | 12/2009 |
| JP | 2011130996 | A | 7/2011 |
| KR | 101644843 | B1 | 8/2016 |
| RS | 20120373 | A1 | 4/2014 |
| WO | 2004100067 | A2 | 11/2004 |
| WO | 2005079658 | A2 | 9/2005 |
| WO | 2010034107 | A1 | 4/2010 |
| WO | 2010036653 | A1 | 4/2010 |
| WO | 2015059700 | A1 | 4/2015 |
| WO | 2015078735 | A1 | 6/2015 |
| WO | 2015110859 | A1 | 7/2015 |
| WO | 2016065411 | A1 | 5/2016 |
| WO | 2016178141 | A1 | 11/2016 |
| WO | 2016209491 | A1 | 12/2016 |
| WO | 2017060463 | A1 | 4/2017 |
| WO | 2017089139 | A1 | 6/2017 |
| WO | 2017100188 | A2 | 6/2017 |
| WO | 2017144934 | A1 | 8/2017 |
| WO | 2018042376 | A1 | 3/2018 |
| WO | 2019094893 | A1 | 5/2019 |
| WO | 2019135877 | A1 | 7/2019 |
| WO | 2019240991 | A1 | 12/2019 |
| WO | 2020033613 | A1 | 2/2020 |
| WO | 2021044240 | A1 | 3/2021 |

OTHER PUBLICATIONS

Romano et al. "Non-contact respiratory monitoring using an RGB camera for real-world applications." Sensors 21.15 (2021): 5126. (Year: 2021).*

Sun et al. "An unobtrusive and non-contact method for respiratory measurement with respiratory region detecting algorithm based on depth images." IEEE Access 7 (2018): 8300-8315. (Year: 2018).*

Sokooti, Hess , et al., "Hierarchical Prediction of Registration Misalignment Using a Convolutional LSTM: Application to Chest CT Scans", IEEE Access, IEEE, USA, vol. 9, Apr. 20, 2021, 62008-62020, 13 pages.

"European Search Report", European Application No. 17156334.9, Applicant: Covidien LP, Aug. 23, 2017, 10 pages.

"European Search Report", European Patent Application No. 17156337.2, Applicant: Covidien LP, Aug. 23, 2017, 10 pages.

"International Search Report and Written Opinion", International Application No. PCT/US2021/015669, Apr. 12, 2021, 15 pages.

"International Search Report and Written Opinion", International Application No. PCT/US2018/060648, Jan. 28, 2019, 17 pages.

"International Search Report and Written Opinion", International Application No. PCT/US2018/065492, Mar. 8, 2019, 12 pages.

"International Search Report and Written Opinion", International Application No. PCT/US2019/035433, Nov. 11, 2019, 17 pages.

"International Search Report and Written Opinion", International Application No. PCT/US2019/045600, Oct. 23, 2019, 19 pages.

"Invitation to Pay Additional Fees and Partial International Search Report", International Application No. PCT/US2019/035433, Sep. 13, 2019, 16 pages.

"Medical Electrical Equipment, Part 2-61: Particular requirements for basic safety and essential performance of pulse oximeter equipment", BSI Standards Publication, BS EN ISO 80601-2-61, 2011, 98 pages.

Aarts, Lonneke A.M., et al., "Non-contact heart rate monitoring utilizing camera photoplethysmography in neonatal intensive care unit—A Pilot Study", Early Human Development 89, 2013, pp. 943-948, 6 pages.

Abbas, A.K. , et al., "Neonatal non-contact respiratory monitoring based on real-time infrared thermography", Biomed. Eng. Online, vol. 10, No. 93, 2011, 17 pages.

Addison, Paul S., "A Review of Signal Processing Used in the Implementation of the Pulse Oximetry Photoplethysmographic Fluid Responsiveness Parameter", International Anesthesia Research Society, vol. 119, No. 6, Dec. 2014, pp. 1293-1306, 14 pages.

Addison, Paul S., et al., "Developing an algorithm for pulse oximetry derived respirator rate (RRoxi): a healthy volunteer study", J Clin comput, No. 26, 2012, pp. 45-51, 7 pages.

Addison, Paul S., et al., "Pulse oximetry-derived respiratory rate in general care floor patients", J. Clin Monit Comput, No. 29, 2015, pp. 113-120, 8 pages.

Addison, P.S., et al., "Video-based Heart Rate Monitoring across a Range of Skin Pigmentations during an Acute Hypoxic Challenge", J Clin Monit Comput, vol. 9, Nov. 9, 2017, 15 pages.

Al-Naji, Ali , et al., "Real Time Apnoea Monitoring of Children Using the Microsoft Kinect Sensor: A Pilot Study", Sensors, 17(286), Feb. 3, 2017, 15 pages.

(56) References Cited

OTHER PUBLICATIONS

Amazon , "Dockem Koala Tablet Wall Mount Dock for ipad Air/Mini/Pro, Samsung Galaxy Tab/Note, Nexus 7/10, and More (Black Brackets, Screw-in Version)", https://www.amazon.com/Tablet-Dockem-Samsung-Brackets-Version-dp/ B00JV75FC6?th=1, First available Apr. 22, 2014, viewed on Nov. 16, 2021, Apr. 22, 2014, 4 pages.
Amelard , et al., "Non-contact transmittance photoplethysmographic imaging (PPGI) for long-distance cardiovascular monitoring", ResearchGate, XP055542534 [Retrieved online Jan. 15, 2019], Mar. 23, 2015, pp. 1-13, 14 pages.
Armanian, A. M. , "Caffeine administration to prevent apnea in very premature infants", Pediatrics & Neonatology, 57 (5), 2016, pp. 408-412, 5 pages.
Barone, S, et al., "Computer-aided modelling of three-dimensional maxillofacial tissues through multi-modal imaging", Proceedings of the Institution of Mechanical Engineers, Journal of Engineering in Medicine, Part H vol. 227, No. 2, Feb. 1, 2013, 1 page.
Barone, S , et al., "Creation of 3D Multi-body Orthodontic Models by Using Independent Imaging Sensors", Senros MDPI AG Switzerland, vol. 13, No. 2, Jan. 1, 2013, pp. 2033-2050, 18 pages.
Bartula, M. , et al., "Camera-based System for Sontactless Monitoring of Respiration", 2013 35th Annual International Conference of the IEEE Engineering in Medicine and Biology Society (EMBC), Jul. 3, 2013, pp. 2672-2675, 4 pages.
Bhattacharya, S. , et al., "A Novel Classification Method for Predicting Acute Hypotensive Episodes in Critical Care", 5th ACM Conference on Bioinformatics, Computational Bilogy and Health Informatics (ACM-BCB 2014), Newport Beach, USA, 2014, 10 pages.
Bhattacharya, S. , et al., "Unsupervised learning using Gaussian Mixture Copula models", 21st International Conference on Computational Statistics (COMPSTAT 2014), Geneva, Switzerland, 2014, pp. 523-530, 8 pages.
Bickler, Philip E., et al., "Factors Affecting the Performance of 5 Cerebral Oximeters During Hypoxia in Healthy Volunteers", Society for Technology in Anesthesia, vol. 117, No. 4, Oct. 2013, pp. 813-823, 11 pages.
Bousefsaf, Frederic , et al., "Continuous wavelet filtering on webcam photoplethysmographic signals to remotely assess the instantaneous heart rate", Biomedical Signal Processing and Control 8, 2013, pp. 568-574, 7 pages.
Bruser, C. , et al., "Adaptive Beat-to-Beat Heart Rate Estimation in Ballistocardiograms", IEEE Transactions Information Technology in Biomedicine, vol. 15, No. 5, Sep. 2011, pp .. 778-786, 9 pages.
Cennini, Giovanni , et al., "Heart rate monitoring via remote photoplethysmography with motion artifacts reduction", Optics Express, vol. 18, No. 5, Mar. 1, 2010, pp. 4867-4875, 9 pages.
Colantonio, S. , et al., "A smart mirror to promote a healthy lifestyle", Biosystems Engineering. vol. 138, Innovations in Medicine and Healthcare, Oct. 2015, pp. 33-43, 11 pages.
Cooley , et al., "An Alorithm for the Machine Calculation of Complex Fourier Series", Aug. 17, 1964, pp. 297-301, 5 pages.
Di Fiore, J.M. , et al., "Intermittent hypoxemia and oxidative stress in preterm infants", Respiratory Physiology & Neurobiology, No. 266, 2019, pp. 121-129, 25 pages.
Fei, J. , et al., "Thermistor at a distance: unobtrusive measurement of breathing", IEEE Transactions on Biomedical Engineering, vol. 57, No. 4, 2010, pp. 968-998, 11 pages.
Feng, Litong , et al., "Dynamic ROI based on K-means for remote photoplethysmography", IEE International Conference on Accoustics, Speech and Signal Processing (ICASSP), Apr. 2015, pp. 1310-1314, 5 pages.
Fischer , et al., "ReMoteCare: Health Monitoring with Streaming Video", OCMB '08, 7th International Conference on Mobile Business, IEEE, Piscataway, NJ,, Jul. 7, 2008, pp. 280-286.
George , et al., "Respiratory Rate Measurement From PPG Signal Using Smart Fusion Technique", International Conference on Engineering Trends and Science & Humanities (ICETSH-2015), 2015, 5 pages.
Goldman, L.J. , "Nasal airflow and thoracoabdominal motion in children using infrared thermographic video processing", Pediatric Pulmonology, vol. 47, No. 5, 2012, pp. 476-486, 11 pages.
Grimm, T. , et al., "Sleep position classification from a depth camera using bed aligned maps", 23rd International Conference on Pattern Recognition (ICPR), Dec. 2016, pp. 319-324, 6 pages.
Gsmarena , "Apple iPad Pro 11 (2018)", https://www.gsmarena.com/apple_ipad_pro_11_(2018)-9386.pjp, viewed on Nov. 16, 2021, 1 page.
Guazzi, Alessandro R., et al., "Non-contact measurement of oxygen saturation with an RGB camera", Biomedical Optics Express, vol. 6, No. 9, Sep. 1, 2015, pp. 3320-3338, 19 pages.
Han, J. , et al., "Visible and infrared image registration in man-made environments employing hybrid visuals features", Pattern Recognition Letters, vol. 34, No. 1, 2013, pp. 42-51, 10 pages.
Harte, James M., et al., "Chest wall motion analysis in healthy volunteers and adults with cystic fibrosis using a novel Kinect-based motion tracking system", Medical & Biological Engineering & Computing, 54(11), Feb. 13, 2016, pp. 1631-1640, 11 pages.
Huddar, V. , et al., "Predicting Postoperative Acute Respiratory Failure in Critical Care using Nursing Notes and Physiological Signals", 36th Annual International Conference of IEEE Engineering in Medicine and Biology Society (IEEE EMBC 2014), Chicago, USA, 2014, pp. 2702-2705, 4 pages.
Hyvarinen, A. , et al., "Independent Component Analysis: Algorithms and Applications", Neural Networks, vol. 13, No. 4, 2000, pp. 411-430, 31 pages.
Javadi, M. , et al., "Diagnosing Pneumonia in Rural Thailand: Digital Cameras versus Film Digitizers for Chest Radiograph Teleradiology", International Journal of Infectious Disease, 10(2), Mar. 2006, pp. 129-135, 7 pages.
Jopling, M. W., et al., "Issues in the Laboratory Evaluation of Pulse Oximeter Performance", Anesth. Analg., No. 94, 2002, pp. S62-S68, 7 pages.
Kastle, Siegfried W., et al., "Determining the Artifact Sensitivity of Recent Pulse Oximeters During Laboratory Benchmarking", Journal of Clinical Monitoring and Computing, vol. 16, No. 7, 2000, pp. 509-552, 14 pages.
Klaessens, J.H.G.M. , et al., "Non-invasive skin oxygenation imaging using a multi-spectral camera system: Effectiveness of various concentration algorithms applied on human skin", Proc. of SPIE, vol. 7174 717408-1, 2009, 14 pages.
Kong, Lingqin , et al., "Non-contact detection of oxygen saturation based on visible light imaging device using ambient light", Optics Express, vol. 21, No. 15, Jul. 29, 2013, p. 17646-17471, 8 pages.
Kortelainen, J.M. , et al., "Sleep staging based on signals acquired through bed sensor", IEEE Transactions on Informational Technology in Biomedicine, vol. 14, No. 3, May 2010, pp. 776-785, 10 pages.
Kumar, M. , et al., "Distance PPG: Robust non-contact vital signs monitoring using a camera", Biomedical Optics Express, vol. 6, No. 5, May 1, 2015, 24 pages.
Kwon, Sungjun , et al., "Validation of heart rate extraction using video imaging on a built-in camera system of a smartphone", 34th Annual International Conference of the IEEE EMBS, San Diego, CA, USA, Aug. 28-Sep. 1, 2012, pp. 2174-2177, 4 pages.
Lai, C.J. , et al., "Heated humidified high-flow nasal oxygen prevents intraoperative body temperature decrease in non-intubated thoracoscopy", Journal of Anesthesia, Oct. 15, 2018, 8 pages.
Lawrence, E. , et al., "Data Collection, Correlation and Dissemination of Medical Sensor information in a WSN", IEEE 2009 Fifth International Conference on Networking and Services, 978-0-7695-3586-9/09, Apr. 20, 2009, pp. 402-408, 7 pages.
Li , et al., "A Non-Contact Vision-Based System for Respiratory Rate Estimation", IEEE 978-1-4244-7929-0/14, 2014, pp. 2119-2122, 4 pages.
Liu, H. , et al., "A Novel Method Based on Two Cameras for Accurate Estimation of Arterial Oxygen Saturation", BioMedical Engineering Online, vol. 14, No. 52, 2015, 18 pages.
Liu, S. , et al., "In-bed pose estimation: Deep learning with shallow dataset. IEEE journal of translational engineering in health and medicine", IEEE Journal of Translational Engineering in Health and Medicine, No. 7, 2019, pp. 1-12, 12 pages.

(56) References Cited

OTHER PUBLICATIONS

Liu, C. , et al., "Motion Magnification", ACM Transactions on Graphics (TOG), vol. 24, No. 3, 2005, pp. 519-526, 8 pages.
Lv, et al., "Class Energy Image Analysis for Video Sensor-Based Gait Recognition: A Review", Sensors, No. 15, 2015, pp. 932-964, 33 pages.
Mcduff, Daniel J., et al., "A Survey of Remote Optical Photoplethysmographic Imaging Methods", IEEE 987-1-4244-0270-1/15, 2015, pp. 6398-6404, 7 pages.
Mestha, L.K. , et al., "Towards Continuous Monitoring of Pulse Rate in Neonatal Intensive Care Unit with a Webcam", Proc. of 36th Annual Int. Conf. of the IEEE Engineering in Medicine and Biology Society, Chicago, IL, 2014, pp. 3817-3820, 4 pages.
Mukherjee, S. , et al., "Patient health management system using e-health monitoring architecture", IEEE, International Advance Computing Conference (IACC), 978-1-4799-2572-8/14, Feb. 21, 2014, pp. 400-405, 6 pages.
Nguyen , et al., "3D shape, deformation and vibration measurements using infrared Kinect sensors and digital image correlation", Applied Optics, vol. 56, No. 32, Nov. 10, 2017, 8 pages.
Ni , et al., "RGBD-Camera Based Get-Up Event Detection for Hospital Fall Prevention", Acoustics, Speech and Signal Processing (ICASSP) 2012 IEEE International Conf., Mar. 2012, pp. 1405-1408, 6 pages.
Nisar , et al., "Contactless heart rate monitor for multiple persons in a video", IEEE International Conference on Consumer Electronics—Taiwan (ICCE-TW), XP03291229 [Retreived on Jul. 25, 2016], May 27, 2016, 2 pages.
Pereira, C. , et al., "Noncontact Monitoring of Respiratory Rate in Newborn Infants Using Thermal Imaging", IEEE Transactions on Biomedical Engineering, Aug. 23, 2018, 10 pages.
Poh , et al., "Advancements in Noncontact, Multiparameter Physiological Measurements Using a Webcam", IEEE Transactions on Biomedical Engineering, vol. 58, No. 1, Jan. 2011, pp. 7-11, 5 pages.
Poh , et al., "Non-contact, automated cardiac pulse measurements using video imaging and blind source separation", OPT. Express 18, 2010, pp. 10762-10774, 14 pages.
Povsic, Klemen , et al., "Real-Time 3D visualization of the thoraco-abdominal surface during breathing with body movement and deformation extraction", Physiological Measurement, vol. 36, No. 7, May 28, 2015, pp. 1497-1516, 22 pages.
Prochazka , et al., "Microsoft Kinect Visual and Depth Sensors for Breathing and Heart Rate Analysis", Senors, vol. 16, No. 7, Jun. 28, 2016, 11 pages.
Rajan, V. , et al., "Clinical Decision Support for Stroke using Multiview Learning based Models for NIHSS Scores", PAKDD 2016 Workshop: Predictive Analytics in Critical Care (PACC), Auckland, New Zealand, 2016, pp. 190-199, 10 pages.
Rajan, V., et al., "Dependency Clustering of Mixed Data with Gaussian Mixture Copulas", 25th International Joint Conference on Artificial Intelligence IJCAI, New York, USA, 2016, pp. 1967-1973, 7 pages.
Reisner, A. , et al., "Utility of the Photoplethysmogram in Circulatory Monitoring", American Society of Anesthesiologist, May 2008, pp. 950-958, 9 pages.
Reyes, B.A. , et al., "Tidal vol. and Instantaneous Respiration Rate Estimation using a Volumetric Surrogate Signal Acquired via a Smartphone Camera", IEEE Journal of Biomedical and Health Informatics, vol. 21(3), Feb. 25, 2016, pp. 764-777, 15 pages.
Rougier, Caroline , et al., "Robust Video Surveillance for Fall Detection Based on Human Shape Deformation", IEEE Transactions on Circuits and Systems for Video Technology, vol. 21, No. 5, May 2011, pp. 611-622, 12 pages.
Rubinstein, M , "Analysis and Visualization of Temporal Variations in Video", Department of Electrical Engineering and Computer Science, Massachusetts Institute of Technology, Feb. 2014, 118 pages.
Scalise, Lorenzo , et al., "Heart rate measurement in neonatal patients using a webcamera", Department of Industrial Engineering and Mathematical Science, Italy, 978-1-4673-0882-3/12, EEE, 2012, 4 pages.
Schaerer, J. , et al., "Multi-dimensional respiratory motion tracking from markerless optical surface imaging based on deformable mesh registration", Physics in Medicine and Biology, vol. 57, No. 2, Dec. 14, 2011, pp. 357-373, 18 pages.
Sengupta, A. , et al., "A Statistical Model for Stroke Outcome Prediction and Treatment Planning", 38th Annual International Conference of the IEE Engineering in Medicine and Biology (Society IEEE EMBC2016), Orlando, USA, 2016, pp. 2516-2519, 4 pages.
Shah, Nitin , et al., "Performance of three new-generation pulse oximeters during motion and low perfursion in volunteers", Journal of Clinical Anesthesia, No. 24, 2012, pp. 385-391, 7 pages.
Shao, Dangdang , et al., "Noncontact Monitoring Breathing Pattern, Exhalation Flow Rate and Pulse Transit Time", EEE Transactions on Biomedical Engineering, vol. 61, No. 11, Nov. 2014, pp. 2760-2767, 8 pages.
Shrivastava, H. , et al., "Classification with Imbalance: A Similarity-based Method for Predicting Respiratory Failure", IEEE International Conference on Bioinformatics and Biomedicine (IEEE BIBM2015), Washington, DC,USA, 2015, pp. 707-714, 8 pages.
Srinivas, J., et al., "A Mutual Authentication Framework for Wireless Medical Sensor Networks", Journal of Medical Systems, 41:80, 2017, pp. 1-19, 19 pages.
Sun, Yu , et al., "Motion-compensated noncontact imaging photoplethysmography to monitor cardiorespiratory status during exercise", Journal of Biomedical Optics, vol. 16, No. 7, Jul. 1, 2011, 10 pages.
Sun, Yu , et al., "Noncontact imaging photoplethysmography to effectively access pulse rate variability", Journal of Biomedical Optics, vol. 18(6), Jun. 2013, 10 pages.
Tamura , et al., "Wearable Photoplethysmographic Sensors—Past & Present", Electronics, vol. 3, 2014, pp. 282-302, 21 pages.
Tarassenko, L. , et al., "Non-contact video-based vital sign monitoring using ambient light and auto-regressive models", Institute of Physics and Engineering in Medicine, vol. 35, 2014, pp. 807-831, 26 pages.
Teichmann, D. , et al., "Non-Contact monitoring techniques-Principles and applications", In Proc. of IEEE International Conference of the Engineering in Medicine and Biology Society (EMBC), San Diego, CA, 2012, pp. 1302-1305, 4 pages.
Transue, S. , et al., "Real-time Tidal vol. Estimation using Iso-surface Reconstruction", 2016 IEEE First International Conference on Connected Health: Applications, Systems and Engineering Technologies (CHASE), Jun. 27, 2016, pp. 209-218, 10 pages.
Verkruysee, Wim , et al., "Calibration of Contactless Pulse Oximetry", Anesthesia & Analgesia, vol. 124, No. 1, Jan. 2017, pp. 136-145, 10 pages.
Villarroel, Mauricio , et al., "Continuous non-contact vital sign monitoring in neonatal intensive care unit", Healthcare Technology Letters, vol. 1, Issue 3, 2014, pp. 87-91, 5 pages.
Wadhwa, N. , et al., "Phase-Based Video Motion Processing", MIT Computer Science and Artificial Intelligence Lab, Jul. 2013, 9 pages.
Wadhwa, N. , et al., "Riesz pyramids for fast phase-based video magnification", In Proc. of IEEE International Conference on Computational Photography (ICCP), Santa Clara, CA, 2014, 10 pages.
Wang, W. , et al., "Exploiting spatial redundancy of image sensor for motion robust rPPG", IEEE Transactions on Biomedical Engineering, vol. 62, No. 2, 2015, pp. 415-425, 11 pages.
Wu, H.Y. , et al., "Eulerian video magnifcation for revealing subtle changes in the world", ACM Transactions on Graphics (TOG), vol. 31, No. 4, 2012, pp. 651-658, 8 pages.
Wulbrand, H. , et al., "Submental and diaphragmatic muscle activity during and at resolution of mixed and obstructive apneas and cardiorespiratory arousal in preterm infants", Pediatric Research, No. 38(3), 1995, pp. 298-305, 9 pages.
Yu, M.C. , et al., "Noncontact Respiratory Measurement of vol. Change Using Depth Camera", 2012 Annual International Confer-

(56) References Cited

OTHER PUBLICATIONS ence of the IEEE Engeineering in Medicine and Biology Society, Aug. 28, 2012, pp. 2371-2374, 4 pages.
Zaunseder , et al., “Spatio-temporal analysis of blood perfusion by imaging photoplethysmography”, Progress in Biomedical Optics and Imaging, SPIE—International Society for Optical Engineering, vol. 10501, Feb. 20, 2018, 15 pages.
Zhou, J. , et al., “Maximum parsimony analysis of gene copy No. changes in tumor phylogenetics”, 15th International Workshop on Algorithms in Bioinformatics WABI 2015, Atlanta, USA, 2015, pp. 108-120, 13 pages.
Rezaei, Mahdi , et al., “DeepSOCIAL: Social Distancing Monitoring and Infection Risk Assessment in COVID-19 Pandemic”, Applied Sciences, vol. 10, 7514, Oct. 26, 2020, pp. 1-29, 29 pages.
Sathyamoorthy, Adarsh Jagan, et al., “COVID-Robot: Monitoring Social Distancing Constraints in Crowded Scenarios”, Aug. 21, 2020, pp. 1-11, 11 pages.
Liu, X., et al., “An Image Captioning Method for Infant Sleeping Environment Diagnosis”, Springer International Publishing, May 15, 2019, pp. 18-26, 9 pages.

* cited by examiner

TOUCHLESS VOLUME WAVEFORM SAMPLING TO DETERMINE RESPIRATION RATE

CROSS-REFERENCE TO RELATED APPLICATIONS

The present application claims benefit of priority to U.S. Provisional Patent Application No. 63/379,541, entitled "TOUCHLESS VOLUME WAVEFORM SAMPLING TO DETERMINE RESPIRATION RATE" and filed on Oct. 14, 2022, which is specifically incorporated by reference herein for all that it discloses or teaches.

TECHNICAL FIELD

The disclosure relates generally to subject monitoring.

BACKGROUND

Many conventional medical monitors require attachment of a sensor to a patient in order to detect physiologic signals from the patient and transmit detected signals through a cable to the monitor. These monitors process the received signals and determine vital signs such as the patient's respiration rate, pulse rate, arterial oxygen saturation, or other patient parameters.

Other monitoring systems include other types of monitors and sensors, such as electroencephalogram (EEG) sensors, blood pressure cuffs, temperature probes, air flow measurement devices (e.g., spirometer), and others. Some wireless, wearable sensors have also been developed, such as wireless EEG patches and wireless pulse oximetry sensors.

Video-based monitoring is a field of patient monitoring that uses a remote video camera to detect physical attributes of the patient, such as respiratory parameters including respiration rate, tidal volume, minute volume, effort to breathe, activity, etc. This type of monitoring may also be called "non-contact" or "touchless" monitoring in reference to the use of a remote video sensor(s), which does not contact the patient.

SUMMARY

The present disclosure is directed to techniques for non-contact monitoring of a patient to determine physiological and/or contextual parameters such as respiration rate, tidal volume, minute volume, effort to breath, activity, presence in bed, or the like.

The techniques disclosed herein may provide for improved touchless monitoring of a patient, and in particular an improved signal representative of respiration of the patient. A system may, via a display, present to a user an overlay of a region of interest (ROI) in a field of view of a camera system. This ROI may be a fixed portion of the field of view of the camera system which may be stored in memory. The user may use the ROI to position the field of view of at least one camera sensor of the camera system, such as over a chest or a torso of the patient.

The system may determine pixels within image data associated with respiration and determine a bounding box based on the pixels within image data associated with respiration. The system may enlarge that bounding box to better capture depth information relating to a patient, such as depth information relating to the respiration of the patient. The system may determine a sampling region from which the system may sample pixels. The system may determine the sampling region based on an average including the bounding box (optionally enlarged) and at least one previously determined bounding box. The system may determine at least a portion of a volume waveform based at least in part on the sampling region. The system may determine at least one representation parameter (e.g., respiration rate) based on the volume waveform. The system may output, for display, the at least one respiration parameter. In this manner, the system may capture more depth data than if the bounding box itself was used which may improve the determined volume waveform, particularly in situations where there is excessive noise, such as noise caused by patient movement.

One example technique described herein includes determining a respiratory parameter of a patient, by determining depth data between a non-contact patient monitoring system and the patient, over time. The depth data is associated with a region of interest (ROI) on the patient, the ROI having multiple regions and each region having at least one depth data. In this technique, each of the multiple regions in the ROI are analyzed to determine whether respiration is occurring in the analyzed region, and dependent on respiration not occurring in an analyzed region, not including that analyzed region in a visualization mask calculation, and dependent on respiration occurring in an analyzed region, including that analyzed region in the visualization mask calculation. The techniques may include determining a bounding box around the visualization mask, enlarging the bounding box, determining a sampling region, sampling pixel values in the sampling region, determining a volume waveform based at least in part on the sampled pixel values, determining at least one respiration parameter, and outputting, for display, the respiration parameter, such as respiration rate, based on the volume waveform.

In some examples, a system includes at least one camera sensor configured to capture image data associated with a patient; a memory; and processing circuitry coupled to the at least one camera sensor and the memory, the processing circuitry being configured to: obtain the image data; determine a bounding box for the image data based on pixels within the image data associated with respiration; determine a sampling region for the image data, the sampling region being based on an average including the bounding box for the image data and at least one previously determined bounding box; determine at least a portion of a volume waveform based at least in part on the sampling region; determine at least one respiration parameter based on the volume waveform, and output, for display, the at least one respiration parameter.

In some examples, a method includes obtaining image data from at least one camera sensor; determining a visualization mask based on pixels within the image data associated with respiration; determining a bounding box for the image data based on the visualization mask; determining a sampling region for the image data, the sampling region being based on an average of the bounding box and at least one previously determined bounding box; determining at least a portion of a volume waveform based at least in part on the sampling region; determining at least one respiration parameter based on the volume waveform; and outputting, for display, the at least one respiration parameter.

In some examples, a non-transitory computer-readable storage medium stores instructions, which when executed, cause processing circuitry to obtain image data from at least one camera sensor; determine a visualization mask based on pixels within the image data associated with respiration; determine, based on pixels within the image data associated with respiration, a bounding box for the image data; determine a sampling region for the image data, the sampling region being based on an average of the bounding box for the image data and at least one previously determined bounding box; determine at least a portion of a volume waveform based at least in part on the sampling region; determine at least one respiration rate based on the volume waveform; and output, for display, the at least one respiration parameter based on the volume waveform.

This summary is intended to provide an overview of the subject matter described in this disclosure. This summary is not intended to provide an exclusive or exhaustive explanation of the apparatus and methods described in detail within the accompanying drawings and description below. The details of one or more aspects of the disclosure are set forth in the accompanying drawings and the description below.

DETAILED DESCRIPTION

Figure 1:
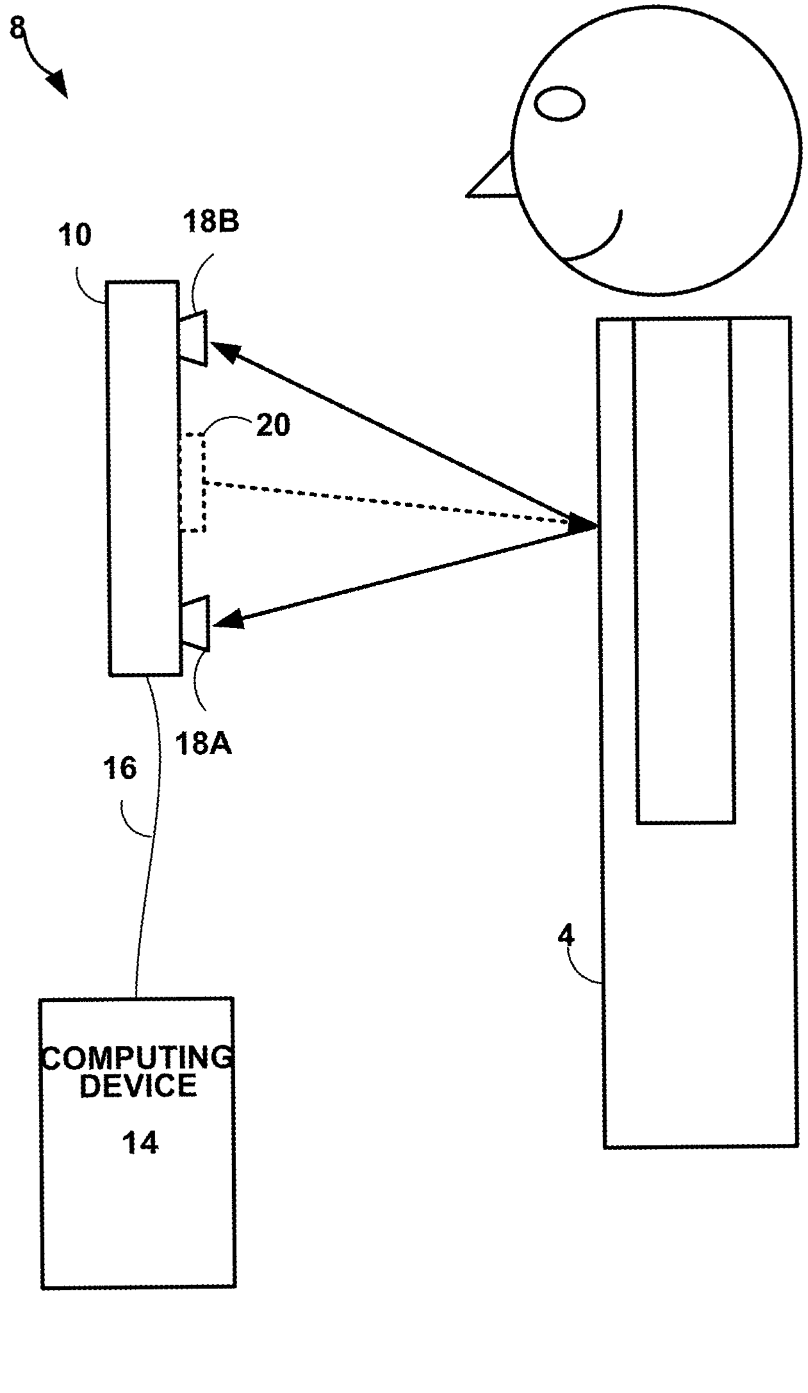
FIG. 1 is a conceptual diagram illustrating an example touchless system for monitoring patient parameters.

As described above, the present disclosure is directed to medical monitoring, and in particular, non-contact, video-based monitoring of respiratory parameters, including respiration rate, tidal volume, minute volume, oxygen saturation, and other parameters such as motion or activity. Systems and techniques are described for obtaining image data, identifying a physiologically relevant area within the video image (e.g., a chest or torso of the patient) and/or determining a bounding box based on pixels within the image data associated with respiration, enlarging the bounding box, determining a sampling region, sampling each pixel value within the sampling region, determining a volume waveform based on the sample pixel values within the sampling region, determining at least one patient parameter based on the volume waveform, and outputting, for display, the at least one patient parameter based on the volume waveform. In this manner, the system may produce a volume waveform having less noise than if the volume waveform was formed based on pixel data solely within the visualization mask area, resulting in a more accurate representation of the patient parameter.

Non-contact or remote monitoring, such as video-based monitoring, can deliver significant benefits over contact monitoring. Some video-based monitoring techniques can reduce cost and waste by reducing use of disposable contact sensors, replacing them with reusable camera systems. Video monitoring may also reduce the spread of infection, by reducing physical contact between caregivers and patients. Video cameras can improve patient mobility and comfort, by freeing patients from wired tethers or bulky wearable sensors. In some cases, these systems can also save time for caregivers, who no longer need to reposition, clean, inspect, or replace contact sensors or manually determine patient parameters such as respiration rate by physically viewing the breathing process of the patient.

One challenge with video or camera monitoring is noise, such as noise due to movement of the patient. For example, when the patient moves, the area being monitored by camera system, such as a visualization mask, may no longer be directed to a portion of the patient associated with respiration. This may create noise in a volume waveform created based on pixel data captured within the visualization mask. A volume waveform may be a waveform that is indicative of a volume, such as a volume of lung(s) of a patient over time. Other potential sources of noise include other people moving within the scene, limited accuracy of a depth camera, environmental noise, or the like. For example, patient movement, movement of others, limited accuracy of depth data, environmental noise, or the like, may cause noise that may corrupt or otherwise obscure depth data indicative of respiration of a patient, making it more difficult to determine patient parameters, such as a respiration rate based on changes in the depth data over time. The present disclosure describes techniques for addressing this motion noise and other noise so as to improve an accuracy or quality of a volume waveform and thereby, the accuracy or quality of a representation of at least one patient parameter based on the volume waveform.

The present disclosure describes techniques for non-contact monitoring of a patient to determine respiratory parameters such as respiration rate, tidal volume, minute volume, oxygen saturation, and other parameters such as motion and activity. The systems and techniques capture image data which may include frames of video of an area of the patient and from that image data determine a volume signal from distance or depth information, and output a representation of the patient parameter(s) based on the volume signal.

A depth sensing feature may provide a measurement of the distance or depth between the detection system and the patient. One or more video cameras may be used to determine the depth, and change in depth, from the system to the patient. For example, when two cameras, set at a fixed distance apart, are used, they offer stereo vision due to the slightly different perspectives of the scene from which distance information is extracted. When distinct features are present in the scene, the stereo image algorithm can find the locations of the same features in the two image streams. However, if an object is featureless (e.g., a smooth surface with a monochromatic color), then the depth camera system has difficulty resolving the perspective differences. By optionally including projector device to project features (e.g., in the form of dots, pixels, lines, etc.) onto the scene, this projected feature can be monitored over time to produce an estimate of changing distance or depth.

In the following description, reference is made to the accompanying FIGS. that form a part hereof and in which is shown by way of illustration at least one specific example. The following description provides additional specific examples. It is to be understood that other examples are contemplated and may be made without departing from the scope or spirit of the present disclosure. The following detailed description, therefore, is not to be taken in a limiting sense. While the present disclosure is not so limited, an appreciation of various aspects of the disclosure will be gained through a discussion of the examples, including the figures, provided below.

FIG. 1 is a conceptual diagram illustrating an example touchless system for monitoring patient parameters. System 8 may include camera system 10 and computing device 14. While shown as two separate devices, in some examples, camera system 10 and computing device 14 may be housed within a single housing. Camera system 10 may be housed within a single housing, as shown, or within a plurality of housings. Camera system 10 may include one or more camera sensors (e.g., camera sensors 18A and 18B) and, in some examples, include projection device 20 which may project dots or lines onto a surface of patient 4 for easier tracking of movement areas of patient 4 associated with respiration. Camera sensors 18A and 18B may be configured to capture pixel data from patient 4. In some examples, camera system 10 may include one or more depth camera sensors (or a plurality of camera sensors that may function as one or more depth camera sensors), one or more red-blue-green camera sensor, or any other type of camera sensor. In some examples, camera system 10 may include one or more depth camera sensors, red-blue-green (RGB) camera sensor, or any other type of camera sensor. In some examples, camera system 10 may be configured to capture image data even if the room in which patient 4 is located is dark.

Camera system 10 may be communicatively coupled to computing device 14 through link 16. Link 16 may be a wired, wireless, or optical connection. In some examples, camera system 10 may be fixedly mounted to a specific location in a room of a hospital or another health care facility, such as on the ceiling of the room. In other examples, camera system 10 may be mounted to an arm of a device configured to pivot such that camera system 10 may be moved away from patient 4 when not in use. In some examples, camera system 10 may be located at a predetermined distance from patient 4 or a bed upon which patient 4 may be located when in use, such as 1 meter, 1.1 meters, 1.2 meters, 1.3 meters, 1.4 meters, 1.5 meters, or the like.

When in use, camera system 10 may be generally aimed toward the chest or torso of patient 4. Camera sensors 18A and 18B may capture image data from patient 4. Such image data may be indicative of various patient parameters, such as respiration rate, tidal volume, minute volume, effort to breath, activity, presence in bed, or the like.

Computing device 14 may generate a volume waveform by determining changes in volume in a depth map, for example. Such changes may be sampled from different regions in the depth map. For example, the computing device 14 may sum all the changes in a whole scene within the field of view of camera system 10. For example, computing device 14 (or camera system 10) may determine a depth map for a first frame of image data of the whole scene within the field of view and a depth map for a second frame of image data of the whole scene within the field of view. Computing device 14 may determine the changes between each entry of the first depth map and corresponding entries in the second depth map. Computing device 14 may sum up the determined changes between the first and second depth map and use the sum of the changes to plot a point of a volume waveform. Computing device 14 may repeat this process with the second depth map and a third depth map, and so on to generate the volume waveform. In some examples, this technique accumulates all the noise within the field of view of camera system 10. As discussed above, movement of the patient, movement of other people, limited accuracy of a depth camera, environmental noise, may cause noise in the depth data. By using the entire field of view (e.g., entire frames of image data), the amount of noise may be much greater than if the depth maps and/or depth data were limited to a smaller region within patient.

Alternatively, computing device 14 may sum up all of the changes of depth data between frames of the image data that are within a fixed region of interest (ROI 310—e.g., the area within the brackets of FIG. 3A) to determine a volume waveform. This fixed ROI may be stored in memory of computing device 14. Such a volume waveform may be of higher quality than the waveform based on all changes between frames of image data within the entire field of view of camera system 10, but may still pick up noise at the edges of the ROI. Alternatively, computing device 14 may sample depth data only from within a visualization mask (e.g., visualization mask 300 of FIGS. 3B-3D), such as an area of images of patient 4 in which there is movement associated with respiration. However, each of these techniques has disadvantages. The techniques of this disclosure may improve the quality of the waveform, which, in some examples, may include combining aspects of such techniques.

For example, computing device 14 may obtain image data. Computing device 14 may determine an ROI. Computing device 14 may determine a bounding box based on pixels within the image data associated with respiration. Computing device 14 may enlarge the bounding box. If the bounding box is too small, (e.g., the bounding box is smaller than a set size) computing device 14 may use the ROI region as the bounding box (e.g., determine the bounding box to be equal to the ROI). In some examples, computing device 14 may add a margin to the bounding box to make the bounding box larger. In this manner, computing device 14 may ensure that the whole of a torso of patient 4 is used in the determination of the volume waveform. In some examples, computing device 14 may determine a plurality of bounding boxes, including wherein each bounding box is determined using a different method, and combine the plurality of bounding boxes in a manner to determine an enlarged bounding box. If the enlarged bounding box is too large (e.g., the enlarged bounding box extends beyond the ROI), computing device 14 may trim the bounding box to fit within the fixed ROI on the screen. Computing device 14 may determine a sampling region, the sampling region being based on an average of the enlarged bounding box and at least one previously determined bounding box. Computing device 14 may determine at least a portion of a volume waveform based on the sampled pixel values within the sampling region. Computing device 14 may determine at least one patient parameter from the volume waveform. Computing device 14 may output, for display, the at least one patient parameter based on the volume waveform.

In such a manner, computing device 14 may sample from the region where respiration can be observed, but with safety checks built in to ensure that if a visualization mask is poor, a bounding box is poor, or either the visualization mask or the bounding box fails completely, then computing device 14 may still create a volume waveform and determine a patient parameter based thereon.

Figure 2:
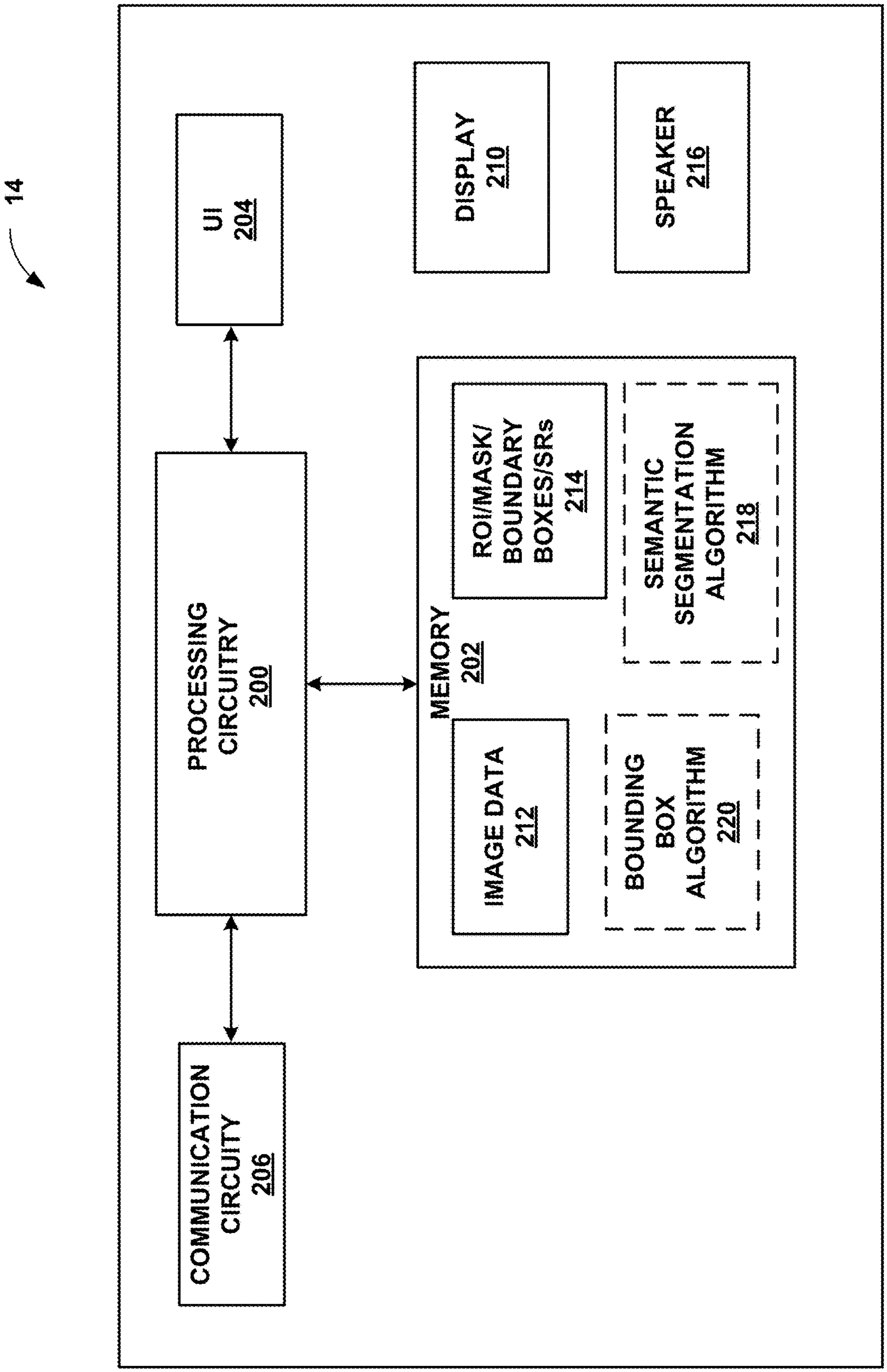
FIG. 2 is a block diagram illustrating an example computing device.

FIG. 2 is a functional block diagram illustrating an example configuration of a computing device 14. In the example of FIG. 2, computing device 14 includes processing circuitry 200, memory 202, user interface (UI) 204, communication circuitry 206, display 210, and speaker 216. In some examples, computing device 14 may be part of or include camera system 10. In some examples, computing device 14 may be a dedicated hardware device with dedicated software for the programming, controlling and/or receiving captured image data from camera system 10. Alternatively, computing device 14 may be a medical computing device that processes received image data, determines one or more patient parameters, such as respiration rate, and displays such parameter(s) via display 210 and/or audibly presents such parameter(s) via speaker 216. In some examples, computing device 14 may be an off-the-shelf computing device, e.g., a laptop computer or smartphone running a mobile application that enables computing device 14 to program, control and/or receive image data from camera system 10.

Memory 202 is configured to store image data captured by camera system 10 in image data 212. Memory 202 is also configured to store an ROI, visualization mask, bounding boxes, and/or sampling regions, in ROI/mask/bounding boxes/SRs 214, which are described in further detail below. For example, an ROI, a visualization mask, a bounding box, an enlarged bounding box, and sampling regions may be stored in ROI/masks/bounding boxes/SRs 214. In some examples, memory 202 is configured to store bounding box algorithm 220 and/or semantic segmentation algorithm 218.

In some examples, a user of computing device 14 may be a clinician, such as a physician, nurse or other healthcare worker. In some examples, display 210 is configured to, under the control of processing circuitry 200, display a measure of one or more patient parameters, such as respiration rate. In addition to or instead of displaying the measure of the one or more parameters, speaker 216, which may include any suitable noise generation circuitry, may output an audible representation of the measure of the one or more parameters.

Processing circuitry 200 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 200 may include multiple components, such as any combination of one or more microprocessors, one or more DSPs, one or more ASICs, or one or more FPGAs, as well as other discrete or integrated logic circuitry, and/or analog circuitry.

Memory 202 may store program instructions, which may include one or more program modules, which are executable by processing circuitry 200. When executed by processing circuitry 200, such program instructions may cause processing circuitry 200 and computing device 14 to provide the functionality ascribed to them herein. The program instructions may be embodied in software, firmware and/or RAMware. Memory 202 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In some examples, processing circuitry 200 of computing device 14 may be configured to provide some or all of the functionality ascribed to computing device 14 and camera system 10. For examples, processing circuitry 200 may determine a region of interest (ROI), such as reading the ROI from memory 202. The ROI may be a set region within the field of view of camera system 10. The ROI may be displayed as a box, brackets, or the like on display 210 overlaid onto image data being captured by camera system 10. The displayed ROI may be used by a user when attempting to line up camera system 10 such that camera sensors 18A and 18B are generally pointed towards an area of patient 4 associated with respiration (e.g., a chest of patient 4). In some examples, processing circuitry 200 may determine a visualization mask. The visualization mask may be a location of a collection of pixels within image data 212 whose changing values over time (e.g., a collocated pixel from one frame of image data 212 to another frame of image data 212) are indicative of changes in respiration volume, such as lung volume.

In order to better account for noise which may be present in image data 212, such as being caused by motion of patient 4, processing circuitry 200 may determine a bounding box. In examples where processing circuitry 200 determines a visualization mask, the bounding box may bound the visualization mask. The bounding box may be a smallest rectangle that includes or covers the entire area of the visualization mask. In some examples, processing circuitry 200 may add a margin to the bounding box to enlarge the bounding box. The enlarged bounding box may be larger than the bounding box and encompass the bounding box. Using an enlarged bounding box may aid in reducing noise when determining a volume signal as movement of patient 4 is less likely to cause areas of image data indicative of volume to move outside of the pixels which may be processed to determine the volume waveform.

In some examples, rather than determine a visualization mask and determine a bounding box as being a smallest rectangle into which the visualization mask may fit (or in conjunction with this process), processing circuitry 200 may execute bounding box algorithm 220 (e.g., the YOLO algorithm) to find an area or item of interest (e.g., a chest or a torso) of patient 4, and then use the output of bounding box algorithm 220 as the position and dimensions of a bounding box. The area or item of interest may be different than the ROI. For example, bounding box algorithm 220 may employ convolution neural networks to identify an area or object of interest (e.g., a chest or a torso) of a person such as patient 4. Bounding box algorithm 220 may be trained to recognize such an area of interest and generate a bounding box around that area of interest. For example, bounding box algorithm 220 may be trained on image data of a plurality of people, such as patients, this image data including the area or object of interest. For example, bounding box algorithm 220 may divide a frame of image data 212 into a plurality of grid cells and use a bounding box regression to determine a bounding box for different classes of items (e.g., a chest or a torso, a bed, a floor, or the like) within the frame of image data 212. Processing circuitry 200 may then use the determined bounding box around the area of interest (e.g., chest or torso) as bounding box (e.g., bounding box 302 in FIG. 3C).

Alternatively, or again in conjunction with other bounding box identification methods, processing circuitry 200 may use semantic segmentation algorithm 218 to identify the torso or chest and determine a visualization mask of the torso or chest of patient 4. For example, semantic segmentation algorithm 218 may be trained on of a plurality of people, such as patients, this image data including the area or object of interest. For example, processing circuitry 200 executing semantic segmentation algorithm 218 may classify a frame of image data 212 as containing an area or item of interest (e.g., a chest or a torso), identify the area or item of interest, and/or determine which pixels belong to that area or item of interest. In some examples, semantic segmentation algorithm 218 may employ a convolutional network to determine a visualization mask of the area or item of interest. Processing circuitry 200 may then determine a bounding box based on the determined visualization mask output from semantic segmentation algorithm 218.

In some examples, processing circuitry 200 may repeat this process periodically, such as during each frame of the image data received. For example, 15 times a second, 30 times a second, 60 times a second, or the like.

Figure 3A:
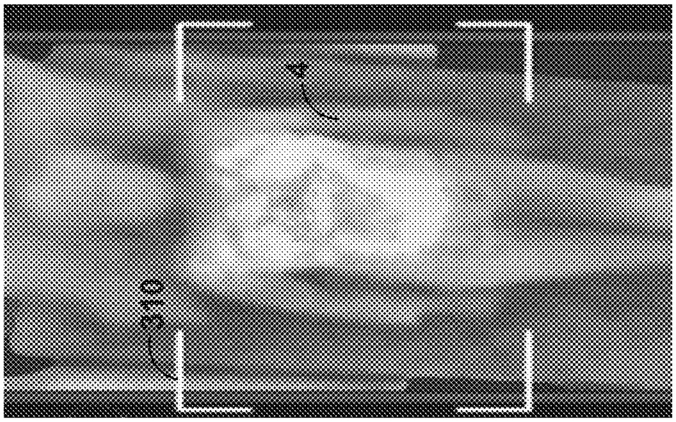
FIGS. 3A-3D are image diagrams illustrating an example visualization mask, bounding box, and enlarged bounding box in accordance with one or more aspects of this disclosure.

FIGS. 3A-3D are image diagrams illustrating an example ROI, visualization mask, bounding box, and enlarged bounding box in accordance with one or more aspects of this disclosure. FIG. 3A shows patient 4 and ROI 310. In some examples, ROI 310 may be brackets (as shown) or a box which may be displayed on display 210 overlayed on image data of patient 4. The overlay of ROI 310 may be used by a user to assist in lining up the field of view of camera system 10 such that areas of patient 4 associated with movement from respiration (e.g., chest or torso) are captured by camera system 10.

Figure 3B:
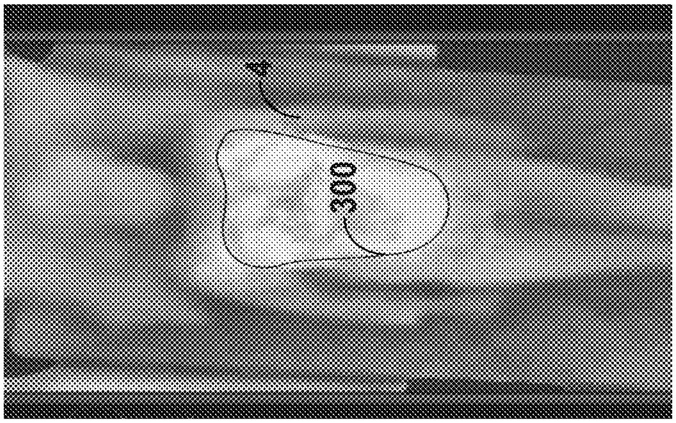

FIG. 3B shows patient 4 and visualization mask 300. In some examples, processing circuitry 200 may generate visualization mask 300 by monitoring pixels within image data 212 over a plurality of frames that are indicative of movement, such as movement associated with respiration, and determine the visualization mask to include such pixels demonstrating movement. Further details on such techniques may be found in U.S. patent application Ser. No. 17/814,798, filed on Jul. 25, 2022, and claiming the benefit of U.S. Provisional Patent Application No. 63/244,331, filed on Sep. 15, 2021, the entire content of both of which is incorporated by reference. In other examples, processing circuitry 200 may determine visualization mask 300 by executing semantic segmentation algorithm 218.

Figure 3C:
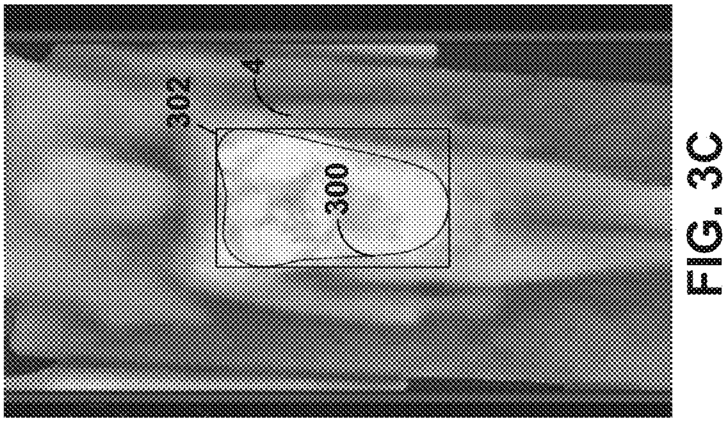

FIG. 3C shows patient 4, visualization mask 300, and bounding box 302. In some examples, bounding box 302 may be the smallest rectangle that includes the entirety of visualization mask 300 as shown. For example, processing circuitry 200 may determine bounding box 302 based on the size and location of visualization mask 300. In some examples, processing circuitry 200 may determine bounding box 302 directly, for example, without basing bounding box 302 on visualization mask 300. For example, processing circuitry 200 may execute bounding box algorithm 220 to determine bounding box 302.

Figure 3D:
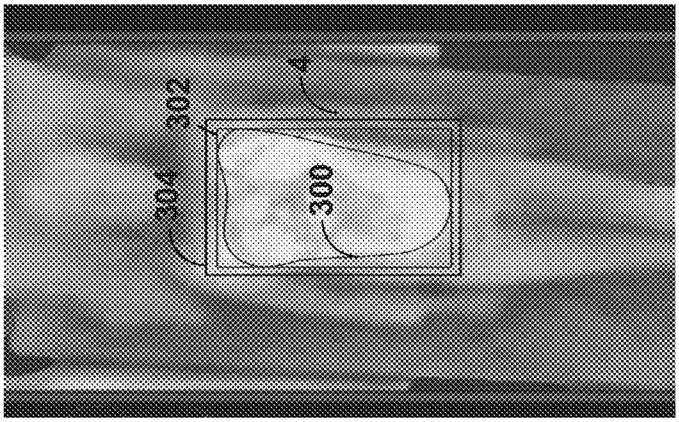

FIG. 3D shows patient 4, visualization mask 300, bounding box 302, and enlarged bounding box 304. In some examples, processing circuitry 200 may determine enlarged bounding box 304 by adding a margin to bounding box 302. In some examples, processing circuitry 200 may add the margin to all four sides of bounding box 302. In some examples, processing circuitry 200 may add the same margin to all four sides of bounding box 302. In some examples, processing circuitry 200 may a different margin to at least one side of bounding box 302 than another side of bounding box 302. In some examples, processing circuitry 200 may add a margin to less than all four sides of bounding box 302. Enlarged bounding box 304 may be used as a basis for a sampling region from which image data is sampled by processing circuitry 200 to determine a volume waveform. In this manner processing circuitry 200 is more likely to use all the pixels which may be indicative of volume than if processing circuitry 200 was to use visualization mask 300 alone as the sampling location, as patient 4 may move and the region of patient 4 indicative of respiration may move outside of visualization mask 300 because enlarged bounding box 304 is larger than visualization mask 300.

In some examples, the margin by which bounding box may be enlarged may be a set number of pixels, such as 5, 10, 15, 20 or the like. In other examples, the margin may be a percentage of a size of bounding box 302. For example, the margin may be 5%, 10%, 15%, 20%, 25% or the like of the size of bounding box 302.

In some examples, rather than, or in addition to, adding a margin to bounding box 302 to determine enlarged bounding box 304, processing circuitry 200 may determine a plurality of bounding boxes, like bounding box 302, and combine the plurality of bounding boxes to determine the enlarged bounding box 304. Such techniques are discussed in more detail with respect to FIG. 5, hereinafter.

Figure 4:
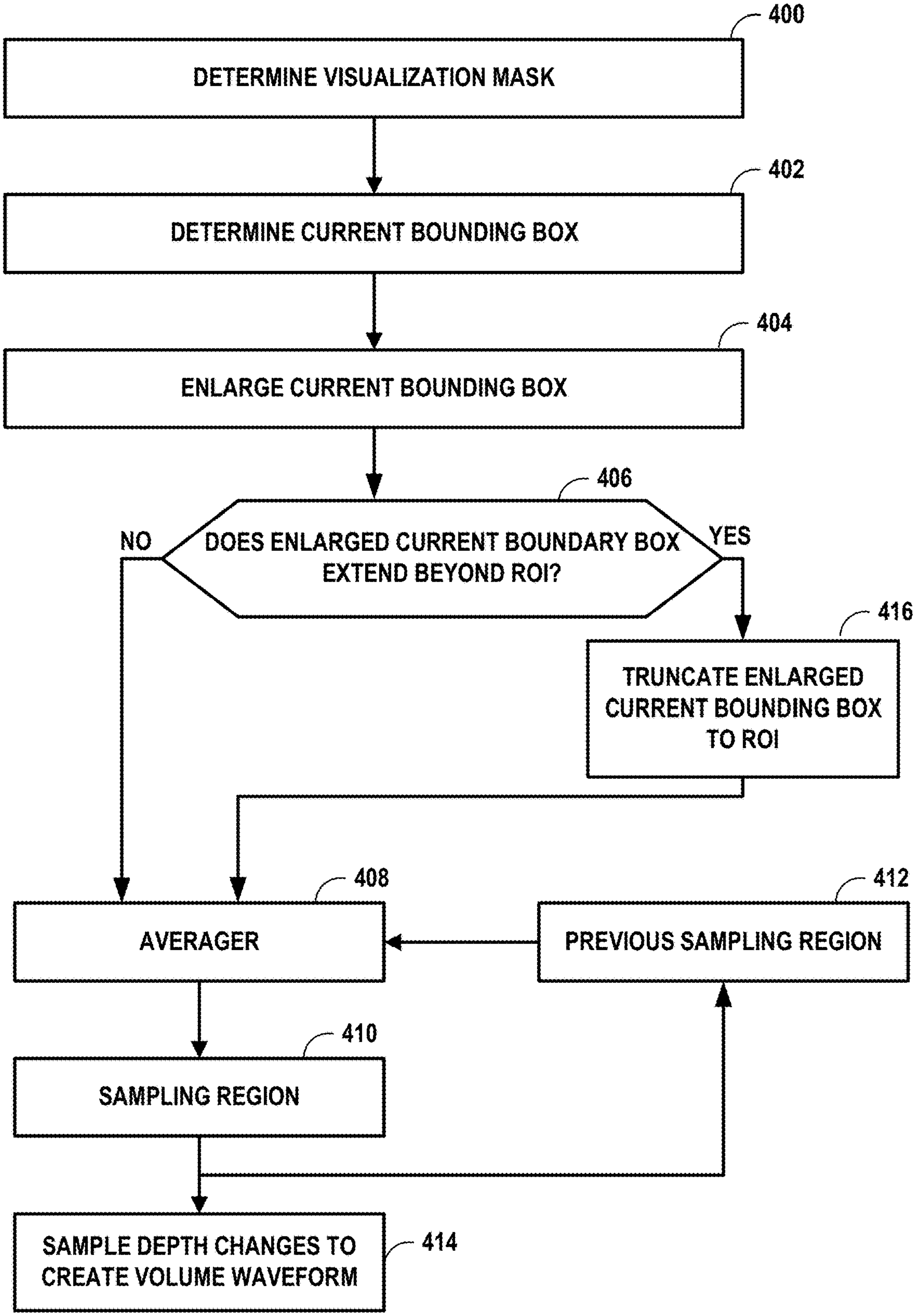
FIG. 4 is a flow diagram illustrating an example volume waveform generation technique in accordance with one or more aspects of this disclosure.

FIG. 4 is a flow diagram illustrating an example volume waveform generation technique in accordance with one or more aspects of this disclosure. Processing circuitry 200 may determine visualization mask 300 (400). For example, processing circuitry 200 may analyze image data received from camera sensors 18A and 18B to determine areas of patient 4 that are indicative of respiration and select such areas as visualization mask 300. Processing circuitry 200 may determine a bounding box (402). For example, processing circuitry 200 may determine bounding box 302 based on a size and a location of visualization mask 300. For example, bounding box 302 may be a smallest rectangle within which all of visualization mask 300 may fit. While the example of FIG. 4 discusses one particular manner in generating a bounding box, such as bounding box 302, other techniques, such as those discussed with respect to FIG. 5, may be used to generate bounding box 302.

Processing circuitry 200 may enlarge the bounding box (404). For example, processing circuitry 200 may add a margin as described with respect to FIG. 3C to bounding box 302 to create enlarged bounding box 304. Processing circuitry 200 may determine whether the enlarged bounding box extends beyond the ROI (406). For example, an enlarged bounding box that extends beyond the ROI may be viewed as too large and may skew the determination of the volume waveform by including pixels from other locations, such as the bed upon which patient 4 may be lying, the floor, or other medical equipment that may be around patient 4. If the enlarged bounding box does extend beyond the ROI (the "YES" path from box 406), processing circuitry 200 may truncate the enlarged bounding box to ROI 310 (416). For example, processing circuitry 200 may set enlarged bounding box 304 to equal ROI 310 or otherwise set enlarged bounding box 304 to not extend beyond ROI 310.

After enlarged bounding box 304 is truncated, processing circuitry 200 may average (408) enlarged bounding box 304 with at least one previously determined bounding box. That is to say, the bounding box 304 based on a current set of image data is combined with at least one bounding box determined based on a previous set of image data. In some examples, averaging may include determining a mean, determining a median, determining a mode, applying a weighted average, taking a maximum or a minimum, determining a sum of absolute differences, or the like. If enlarged bounding box 304 does not extend beyond ROI 310, processing circuitry 200 may leave enlarged bounding box 304 as is and average (408) enlarged bounding box 304 with at least one previously determined bounding box. For example, processing circuitry 200 may determine a moving average of enlarged bounding box 304 and a set number of previously determined bounding boxes (i.e., the 150 bounding boxes determined immediately preceding the current bounding box 304). In another example, the processing circuitry 200 may determine a slow-moving average calculated in accordance with the slow-moving average equation discussed in more detail below. In this aspect, a weighted version of the enlarged bounding box is combined with a weighted calculation taking into account all previously determined bounding boxes (referred to as a previous sampling region (412)).

The averaging may result in a sampling region (410) from which processing circuitry 200 may sample pixel values. For example, processing circuitry 200 may average one or more previous bounding boxes with the current enlarged bounding box to determine a current sampling region. In embodiments where the sampling region is determined using previously determined sampling regions, processing circuitry 200 may store the sampling region for use in averaging with future enlarged bounding boxes (412).

Processing circuitry 200 may sample depth changes to create a volume waveform (414). For example, processing circuitry 200 may determine differences between pixel values of the sampling region versus pixel values of a previous sampling region. Such changes in pixel values may be an indication of respiration and processing circuitry 200 may create the volume waveform based on the changes in pixel values. In some examples, processing circuitry 200 may utilize the volume waveform to calculate a respiration rate and/or other patent parameters and may display the respiration rate and/or other patient parameters on display 210.

In some examples, the computing device may determine a sampling region used to sample depth changes by calculating a slow-moving average, wherein an enlarged bounding box is added to a previously determined sampling region. The slow-moving average can be expressed by the formula: $box_{sampling}=q*mask_{bbox}+(q-1)*box_{previoussampling}$, where $box_{sampling}$ is the sampling region, $mask_{bbox}$ is the bounding box (e.g., enlarged bounding box 304 or bounding box 302), $q<1$, and $box_{previoussampling}$ is the previous sampling region.

For the first image analyzed using the slow-moving average upon commencement of the method described herein, there is no previous sampling region, and so $box_{sampling}=q*mask_{bbox}$ (i.e., the first calculated sampling region is equal to the first determined bounding box multiplied by q). For the second image analyzed, the sampling region is equal to the second determined bounding box multiplied by q plus the previous sampling region multiplied by q−1. Since the previous sampling region was the previous (i.e., first determined) bounding box multiplied by q, the sampling region for the second image analyzed is equal to the second determined bounding box multiplied by q plus the product of q−1 and the previous (i.e., first) bounding box multiplied by q−1. This sequence continues forward with every successive image analyzed, in which case it can be seen that $box_{previoussampling}$ used in the slow-moving average calculation takes into account, to some extent, every previously determined bounding box. This differentiates the slow-moving average from the previously described moving average wherein the sampling region is calculated as the average of the bounding box and a set number of bounding boxes immediately preceding the bounding box. In the moving average method, the oldest bounding boxes are dropped entirely when calculating the sampling region.

With respect to the slow-moving average equation provided above, larger values of q result in quicker updates of the sampling region. In some examples, the value of q equals 0.05, 0.1, 0.15, 0.2, or some other value lower than 1.

In some examples, processing circuitry 200 may determine if a location of visualization mask 300, bounding box 302, or enlarged bounding box 304 has changed too quickly—for example moved from the extreme right to the extreme left of the image in a relatively short period of time (e.g., 0.5 sec, 1 sec, etc.). This may be indicative of an abrupt change of position of patient 4, or in a failure of the visualization algorithm. In such a scenario, processing circuitry 200 may reset the sampling area to ROI 310. Processing circuitry 200 may also set an "invalid flag" of which downstream algorithms may make use (e.g., a respiration rate algorithm that processing circuitry 200 may execute to determine a respiration rate based on the volume waveform). For example, if invalid flag is set, processing circuitry 200 executing the respiration rate algorithm may take any of a number of actions. For example, processing circuitry 200 may stop posting (e.g., outputting) a respiration rate to avoid posting incorrect values. For example, processing circuitry 200 may continue to post or output a current respiration rate value for a period of time or until the invalid flag is no longer present. For example, processing circuitry 200 may continue respiratory rate determinations, but down weight the current estimate of respiration rate if there is an invalid flag (e.g., processing circuitry 200 may assign a lower confidence rating or level which may affect how the current respiration rate value is averaged with previous respiration rate values). For example, processing circuitry 200 may pass-through the invalid flag or may report additional flags based on the invalid flag being present.

In some examples, processing circuitry 200 may combine temporal information on bounding boxes (e.g., calculated in different frames) to determine an estimate of the bounding box confidence. For example, if the bounding box is at the center of the image, during 10 consecutive frames, and there is a significant change of the bounding box (e.g., moved to the top-right corner), processing circuitry 200 may calculate a low confidence for the last bounding box (the one in the top-right corner). Processing circuitry 200 may use this low confidence rating to discard or down-weight the bounding box or sampled values within any sampling region based on such a bounding box or an associated enlarged bounding box, or utilize the confidence information rating for other purposes.

Figure 5:
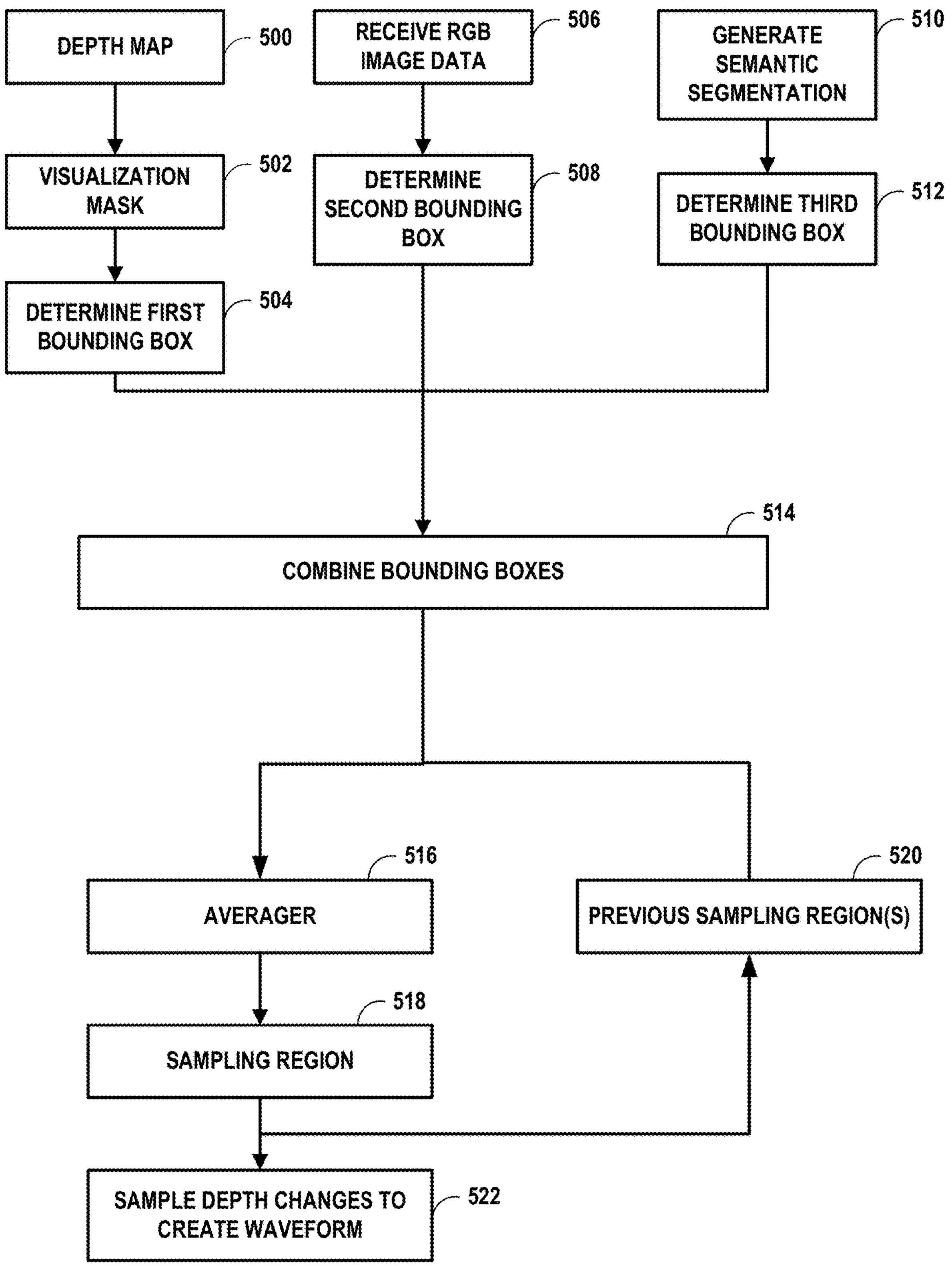
FIG. 5 is a flow diagram illustrating another example volume waveform generation technique in accordance with one or more aspects of this disclosure.

FIG. 5 is a flow diagram illustrating another example volume waveform generation technique in accordance with one or more aspects of this disclosure. In some examples, processing circuitry 200 may determine the enlarged bounding box based on a plurality of bounding boxes, each of the plurality of bounding boxes determined using a different method and/or based on a different set of image data. While the example of FIG. 5 discusses three such bounding boxes (determined using three separate methods), the techniques of this disclosure may apply to two bounding boxes, or more than three bounding boxes. It should be noted that any of the techniques of FIG. 5 may be used to generate the bounding box discussed in the example of FIG. 4.

Processing circuitry 200 may determine a depth map (500). For example, camera system 10 may include at least one depth camera sensor whose output may include a depth map or may be used to determine the depth map. Processing circuitry 200 may determine visualization mask 300 (502). For example, the depth map may include information relating to which pixels in ROI 310 may be indicative of changes in depth, such as movement associated with respiration, and determine visualization mask 300 to include such pixels. Processing circuitry may determine a first bounding box (504). For example, processing circuitry 200 may determine the first bounding box as being the smallest rectangle into which visualization mask 300 fits.

Processing circuitry 200 may also receive red/blue/green (RGB) image data (506) from camera system 10. Processing circuitry 200 may determine a second bounding box (508). For example, processing circuitry 200 may execute a bounding box algorithm, such as YOLO, which may determine the second bounding box based on the received RGB image data.

Processing circuitry 200 may generate a semantic segmentation (510). For example, processing circuitry 200 may associate each pixel within the ROI with a class label, such as a torso, a bed, an arm, a head, or the like. Thus, by using semantic segmentation, processing circuitry 200 may determine an area, e.g., a torso, of patient 4 with which respiration is most likely, which may resemble or result in visualization mask 300. Processing circuitry 200 may determine a third bounding box bounding the area of patient 4 with which respiration is most likely (512). For example, the third bounding box may be a smallest rectangle with which the area with which respiration is most likely as determined by processing circuitry 200 generating the semantic segmentation.

Processing circuitry 200 may combine the plurality of bounding boxes (514) to create a combined bounding box. For example, rather than enlarge any of the first, second or third bounding boxes, processing circuitry 200 may merge the plurality of bounding boxes into a combined bounding box.

In one example, processing circuitry 200 may determine the average centroid and average extent of the plurality of bounding boxes and set this as the bounding box.

Figure 7A:
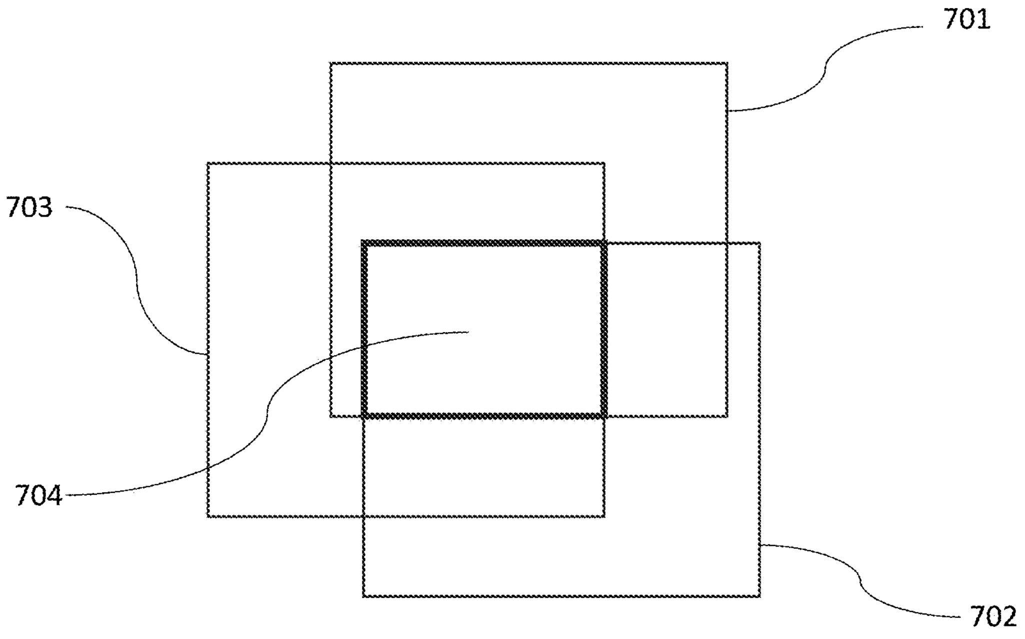
FIGS. 7A-7C are conceptual images illustrating exemplary methods for combining multiple bounding boxes to create a combined bounding box in accordance with one or more aspects of this disclosure.

In another example, processing circuitry 200 may determine a region of overlap of all of the bounding boxes and set this as the bounding box. This is shown in FIG. 7A, wherein a first bounding box 701, a second bounding box 702, and a third bounding box 703 are each determined using different methods for establishing the bounding box. Bounding boxes 701, 702, 703 share common overlap at overlap region 704, and the processing circuitry 200 may set this overlap region 704 as the combined bounding box.

Figure 7B:
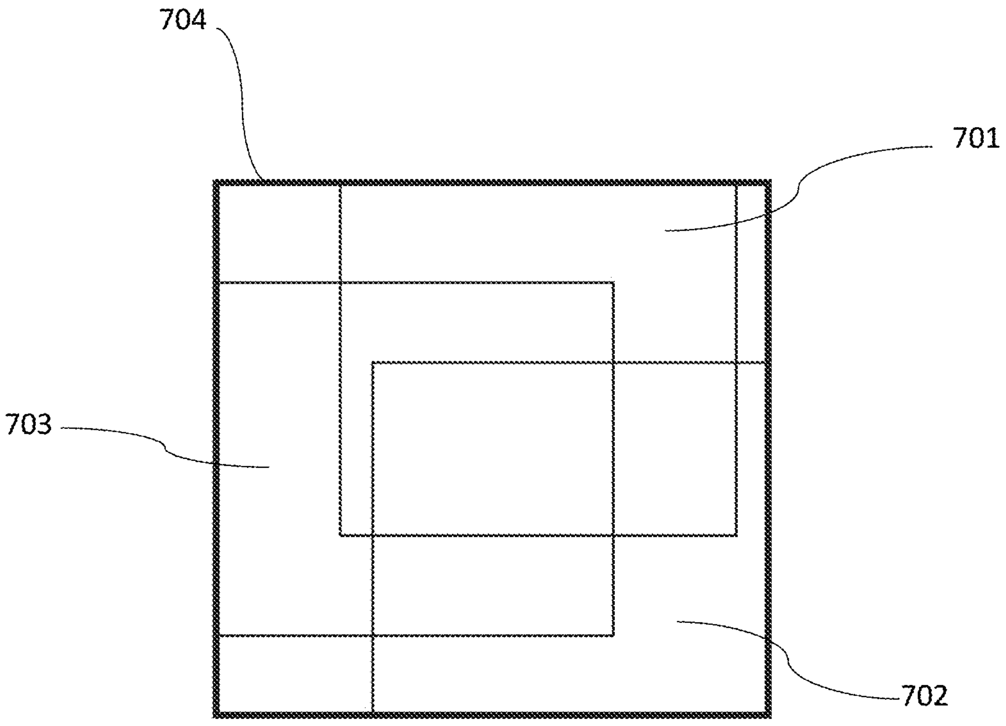

In another example, processing circuitry 200 may determine the superset of all the bounding boxes (e.g., a bounding box around all the individual bounding boxes), and set this as the bounding box. This is shown in FIG. 7B, wherein a first bounding box 701, a second bounding box 702, and a third bounding box 703 are each determined using different methods for establishing the bounding box. The processing circuitry 200 sets as the combined bounding box the superset region 704, the superset region 704 being a rectangle around all of bounding boxes 701, 702, 703. While not shown in FIG. 7B, the superset region 704 can also be set as an irregular shape that follows the outer boundary of the individual boxes.

In another example, processing circuitry 200 may select from the multiple bounding boxes the bounding box having the largest area of the multiple bounding boxes, set this as the bounding box. In this example, smaller bounding boxes are discarded and not used in setting the bounding box.

Figure 7C:
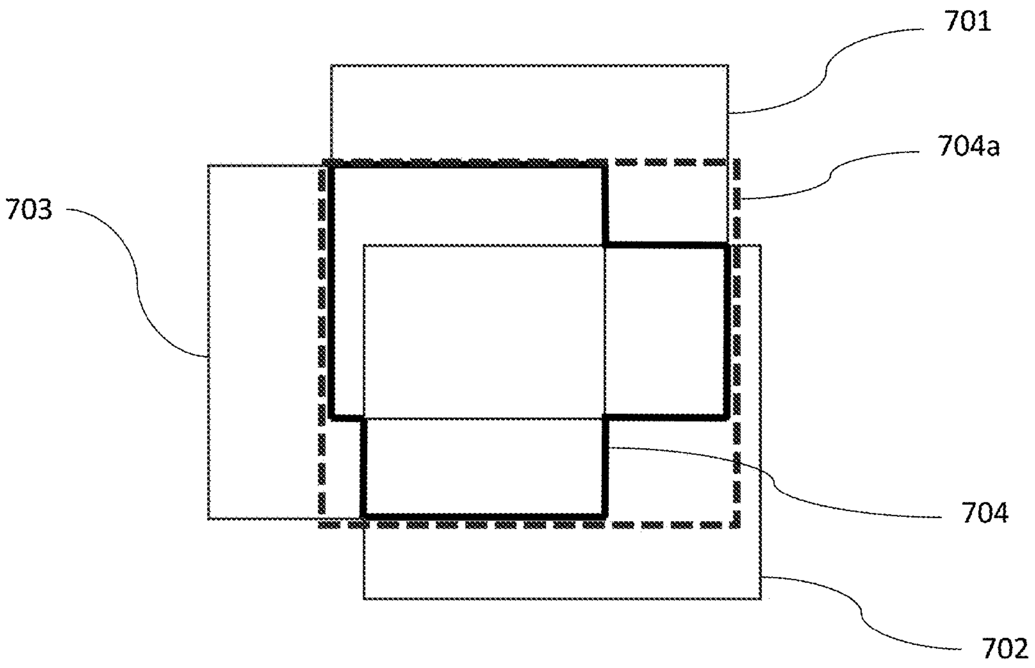

In another example, processing circuitry 200 may utilize majority voting to determine the combined bounding box. For example, if there are more than two bounding boxes, processing circuitry 200 may employ majority voting such that the combined bounding box includes the overlapping area covered by a majority of the plurality of bounding boxes. This example is shown in FIG. 7C, where three bounding boxes 701, 702, 703 are provided. The processing circuitry may merge each area covered by at least two of the three bounding boxes (e.g., a majority) into a combined bounding box, identified as region 704 in FIG. 7C. In this aspect, the combined bounding box may have an irregular (i.e., non-rectangular) shape.

Majority voting may further include a step of resizing the combined bounding box comprised of the merged areas. Processing circuitry 200 may resize region 704 before setting the resized region as the combined bounding box. For example, resized region 704*a* represents a resizing of the region 704 to be the largest rectangle surrounding region 704.

In another example, the processing circuitry 200 may use Non-Maximum Suppression (NMS) to combine the plurality of bounding boxes. NMS is a technique which may be used to select one bounding box out of a plurality of bounding boxes.

While the above examples generally discuss scenarios where three bounding boxes are used to determine a combined bounding box, it should be appreciated that any number of bounding boxes can be used to determine a combined bounding box.

While not shown in the example of FIG. 5, if the combined bounding box (determined by any of the methods described previously) extends beyond the ROI, processing circuitry 200 may truncate the combined bounding box such that the combined bounding box does not extend beyond the ROI, like step 416 of FIG. 4 with respect to the enlarged bounding box.

Processing circuitry 200 may average (516) the combined bounding box with at least one previous bounding box (from box 520). In some examples, averaging may include determining a mean, determining a median, determining a mode, applying a weighted average, taking a maximum or a minimum, determining a sum of absolute differences, or the like. For example, processing circuitry 200 may determine a moving average of the combined bounding box and a set number of the immediately preceding previously determined bounding boxes (some or all of which may also be a combined bounding box). This averaging may result in a sampling region (518) from which processing circuitry 200 may sample pixel values. In embodiments where the sampling region is determined using previously determined sampling regions, processing circuitry 200 may store the sampling region for use in averaging with future enlarged bounding boxes (520).

Processing circuitry 200 may sample depth changes to create a volume waveform (522). For example, processing circuitry 200 may determine differences between pixel values of one frame within the sampling region versus pixel values of another frame within a previous sampling region. Such changes in pixel values may be an indication of respiration and processing circuitry 200 may create the volume waveform based on the changes in pixel values. In some examples, processing circuitry 200 may utilize the volume waveform to calculate a respiration rate and/or other patent parameters and may display the respiration rate and/or other patient parameters on display 210.

Figure 6:
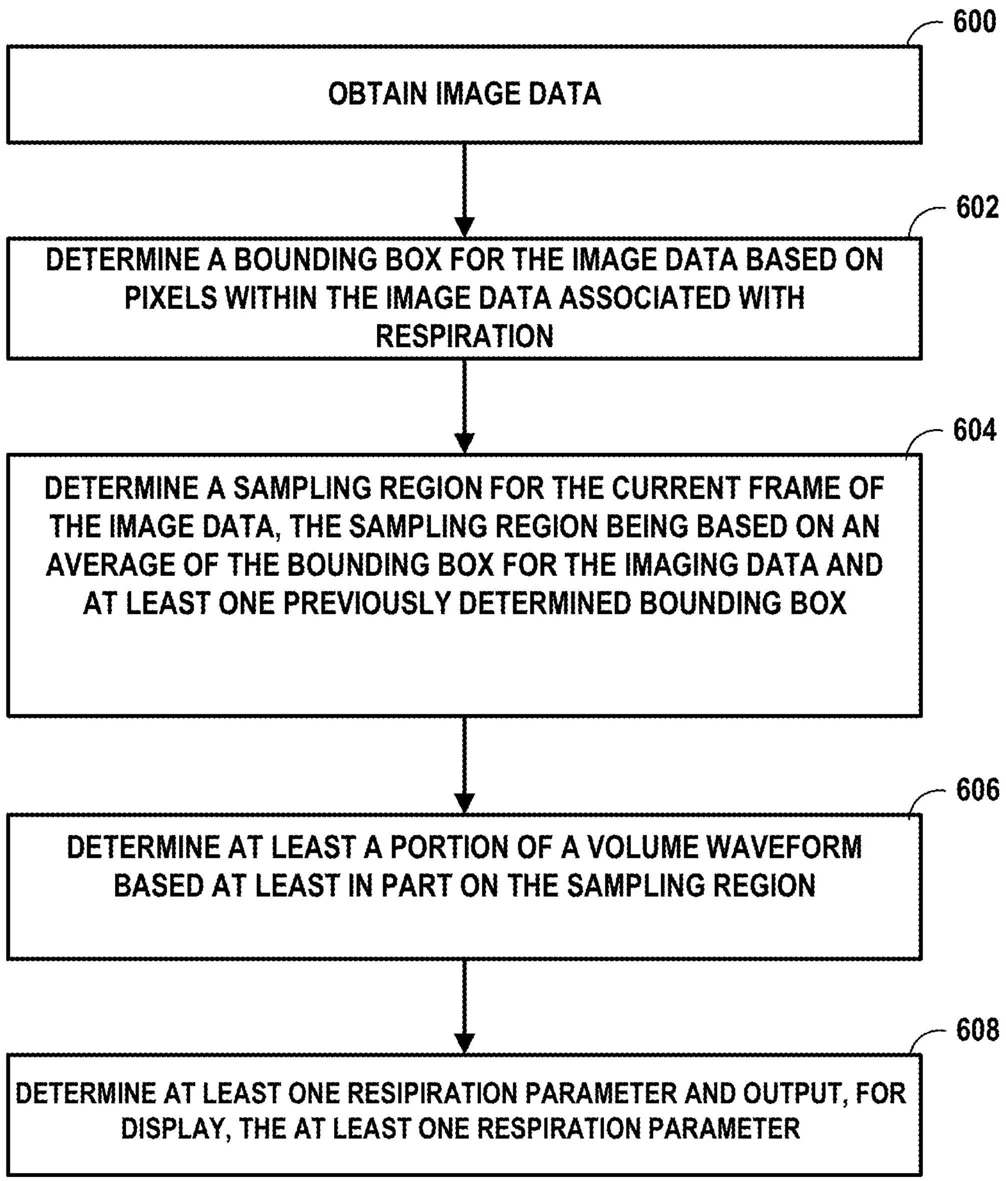
FIG. 6 is a flow diagram illustrating another example volume waveform generation technique in accordance with one or more aspects of this disclosure.

FIG. 6 is a flow diagram illustrating another example volume waveform generation technique in accordance with one or more aspects of this disclosure. Processing circuitry 200 may obtain image data 212 (600). For example, processing circuitry 200 may receive the image data from camera system 10 or retrieve image data 212 from memory 202.

Processing circuitry 200 may determine a bounding box for the image data based on pixels within image data 212 associated with respiration (602). For example, processing circuitry 200 may determine bounding box 302 or enlarged bounding box 304 for the image data. For example, to determine bounding box 302, processing circuitry 200 may at least one of: execute a bounding box algorithm (e.g., the YOLO algorithm); determine visualization mask 300 of pixels associated with respiration based on depth data, wherein bounding box 302 is a smallest rectangle that includes visualization mask 300; or execute a semantic segmentation algorithm to determine visualization mask 300, wherein bounding box 302 is the smallest rectangle that includes visualization mask 300. In some examples, processing circuitry may then enlarge bounding box 302 to generate enlarged bounding box 304. For example, processing circuitry 200 may add a margin of a number of pixels or a percentage of the bounding box 302 as discussed with respect to FIG. 4 or may combine a plurality of bounding boxes as discussed with respect to FIG. 5 to determine the enlarged bounding box 304 (also referred to as a combined bounding box). Enlarged bounding box 304 may be larger than bounding box 302 and encompass bounding box 302.

Processing circuitry 200 may determine a sampling region for the image data, the sampling region being based on an average of enlarged bounding box 304 (or bounding box 302) for the image data and at least one previously determined bounding box (606). For example, processing circuitry 200 may determine $box_{sampling}=q*mask_{bbox}+(q-1)*box_{previoussampling}$, where $box_{sampling}$ is the sampling region, $mask_{bbox}$ is the bounding box (e.g., enlarged bounding box 304 or bounding box 302), $q<1$, and $box_{previoussampling}$ is a previous sampling region.

Processing circuitry 200 may determine at least a portion of a volume waveform based at least in part on the sampling region for the current frame of the image data (608). For example, processing circuitry 200 may determine difference(s) between depth values of pixels within the sampling region (e.g., a sum of those depth values) for the image data and depth values of pixels within a sampling region (e.g., a sum of those depth values) of immediately previous image data. Processing circuitry 200 may determine a point of the volume waveform based on the determined difference(s). For example, processing circuitry 200 may use signal processing techniques to determine depth information over time indicative of changes in volume in the chest area of patient 4. For example, processing circuitry 200 may determine a sum, average, or weighted average of depth information associated with the pixels (e.g., pixel values from a depth map or from a depth camera sensor(s)), and use the changing sum, average or weighted average of the depth information over time (over a plurality of frames of image data) to determine the volume waveform.

Processing circuitry 200 may determine at least one patient parameter, such as a patient respiration parameter, from the volume waveform and output, for display, the at least one patient parameter (610). For example, processing circuitry 200 may output a graphical and/or a numerical representation of the respiration rate of patient 4 to display 210. The graphical representation of the respiration rate of patient 4 may include the volume waveform, itself.

In some examples, processing circuitry 200 may determine ROI 310. For example, ROI 310 may include a predetermined portion of a field of view or generally central portion of a field of view of camera system 10 and may be graphically represented on display 210 to assist a user in lining up camera system 10 with respect to patient 4. In some examples, processing circuitry 200 may retrieve or receive ROI 310 from ROI/mask/bounding boxes/SRs 214 from memory 202 to determine the ROI.

In some examples, processing circuitry 200 may determine that bounding box 302 or enlarged bounding box 304 extends beyond ROI 310. Processing circuitry 200 may, based on bounding box 302 or enlarged bounding box 304 extending beyond ROI 310, set bounding box 302 or enlarged bounding box 304 to equal ROI 310. In some examples, processing circuitry 200 may determine that bounding box 302 or enlarged bounding box 304 is less than a threshold size. Processing circuitry 200 may, based on bounding box 302 or enlarged bounding box 304 being less than the threshold size, set bounding box 302 or enlarged bounding box 304 to be equal to ROI 310. In some examples, the threshold size is a predetermined percentage of ROI 310 such as 5%, 10%, 15%, 20%, 25%, or the like.

In some examples, as part of determining a slow moving average of pixels within the enlarged bounding box, processing circuitry 200 may calculate $box_{sampling}=q*mask_{bbox}+(q-1)*box_{previoussampling}$, where $box_{sampling}$ is the sampling region, $mask_{bbox}$ is the bounding box (e.g., enlarged bounding box 304 or bounding box 302), $q<1$, and $box_{previoussampling}$ is a previous sampling region. In some examples, q is equal to 0.1.

In some examples, processing circuitry 200 may determine that a location of pixels included in at least one of visualization mask 300 or the bounding box (e.g., bounding box 302 or enlarged bounding box 304) have moved more than a predetermined distance from one frame of the image data to another frame of the image data in less than a predetermined time period. In some examples, processing circuitry 200 may, based on the location of pixels of included in the at least one of visualization mask 300 or the bounding box (e.g., bounding box 302 or enlarged bounding box 304) moving more than a predetermined distance from the one frame of the image data to the another frame of the image data in less than a predetermined time period, set the bounding box to equal the ROI.

In some examples, as part of determining bounding box 302, processing circuitry 200 may do at least one of: execute bounding box algorithm 220 to determine the bounding box; determine visualization mask 300 of pixels associated with respiration based on depth data, wherein bounding box 302 is a smallest rectangle that includes the visualization mask; or execute semantic segmentation algorithm 218 to determine visualization mask 300, wherein bounding box 302 is the smallest rectangle that includes visualization mask 300.

In some examples, processing circuitry 200 may add a margin to bounding box 302 (e.g., to generate enlarged bounding box 304). In some examples, processing circuitry 200 may determine a plurality of bounding boxes, and determine the bounding box (e.g., enlarged bounding box 304) based on the plurality of bounding boxes. In some examples, processing circuitry 200 may set the bounding box (e.g., enlarged bounding box 304) to be equal to an average extent of each of the plurality of bounding boxes, set the bounding box to be equal to a majority voted bounding box of the plurality of bounding boxes, set the bounding box to be a largest bounding box of the plurality of bounding boxes, set bounding box to be a superset of the plurality of bounding boxes, or employ non-maximum-suppression to determine the bounding box.

In some examples, processing circuitry 200 may compare the bounding box (e.g., bounding box 302 or enlarged bounding box 304) to a predetermined number of previous bounding boxes, each of the predetermined number of previous bounding boxes being from respective, previous image data captured by at least one camera sensor 18A or 18B. In such examples, processing circuitry 200 may determine a confidence level for the bounding box based on the comparison. In some examples, processing circuitry 200 may determine that the confidence level is relatively low. In some examples, processing circuitry 200 may, based on the confidence level being relatively low, at least one of discard the bounding box, down weight enlarged bounding box 304 (or bounding box 302) when determining a sampling area, or output the confidence level.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the terms "processor" or "processing circuitry" as used herein may refer to one or more of any of the foregoing structures or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including a depth camera, a computing device, an RGB camera, any other camera, or any combination of such devices or apparatuses, an integrated circuit (IC) or a set of ICs, and/or discrete electrical circuitry, residing in any such devices or apparatuses.

This disclosure includes the following examples.

Example 1. A system for non-contact monitoring respiration of a patient comprising: at least one camera sensor configured to capture image data associated with a patient; a memory; and processing circuitry coupled to the at least one camera sensor and the memory, the processing circuitry being configured to: obtain the image data; determine a bounding box for the image data based on pixels within the image data associated with respiration; determine a sampling region for the image data, the sampling region being based on an average of the bounding box for the image data and at least one previously determined bounding box; determine at least a portion of a volume waveform based at least in part on the sampling region; determine at least one respiration parameter based on the volume waveform; and output, for display, the at least one respiration parameter based on the volume waveform.

Example 2. The system of example 1, wherein the processing circuitry is further configured to: determine a region of interest (ROI) of the image data, the ROI comprising a portion of a field of view of the at least one camera sensor; determine that the bounding box extends beyond the ROI; and based on the bounding box extending beyond the ROI, set the bounding box to equal the ROI.

Example 3. The system of example 1, wherein the processing circuitry is further configured to: determine a region of interest (ROI) of the image data, the ROI comprising a portion of a field of view of the at least one camera sensor; determine that the bounding box is less than a threshold size; and based on the bounding box being less than the threshold size, set the bounding box to be equal to the ROI.

Example 4. The system of example 3, wherein the threshold size is a percentage of the ROI.

Example 5. The system of any of examples 1-4, wherein as part of determining the sampling region, the processing circuitry is configured to determine $box_{sampling}=q*mask_{bbox}+(q-1)*box_{previoussampling}$, where $box_{sampling}$ is the sampling region, $mask_{bbox}$ is the bounding box, $q<1$ and $box_{previoussampling}$ is a previous sampling region.

Example 6. The system of example 5, wherein q is equal to 0.1.

Example 7. The system of any of examples 1-6, wherein the processing circuitry is further configured to: determine a region of interest (ROI) of the image data, the ROI comprising a portion of a field of view of the at least one camera sensor; determine that a location of pixels included in at least one of a visualization mask the visualization mask comprising the pixels within the image data associated with respiration, or the bounding box have moved more than a set distance from the image data to previous image data in less than a set time period; and based on the location of pixels of included in the at least one of the visualization mask or the bounding box moving more than a set distance in less than a set time period, set the bounding box to equal the ROI.

Example 8. The system of any of examples 1-7, wherein as part of determining the bounding box, the processing circuitry is configured to at least one of: execute a bounding box algorithm to determine the bounding box; determine a visualization mask, the visualization mask comprising the pixels within the image data associated with respiration, wherein the bounding box is a smallest rectangle that includes the visualization mask; or execute a semantic segmentation algorithm to determine the visualization mask, wherein the bounding box is the smallest rectangle that includes the visualization mask.

Example 9. The system of any of examples 1-7, wherein the processing circuitry is further configured to add a margin to the bounding box.

Example 10. The system of any of examples 1-9, wherein the processing circuitry is further configured to: determine a plurality of bounding boxes; and determine the bounding box based on the plurality of bounding boxes.

Example 11. The system of example 10, wherein as part of determining the bounding box based on the plurality of bounding boxes, the processing circuitry is configured set the bounding box to be equal to an average extent of each of the plurality of bounding boxes, set the bounding box to be equal to a majority voted bounding box of the plurality of bounding boxes, set the bounding box to be a largest bounding box of the plurality of bounding boxes, set the bounding box to be a superset of the plurality of bounding boxes, or employ non-maximum-suppression to determine the bounding box.

Example 12. The system of any of examples 1-11, wherein the processing circuitry is further configured to: compare the bounding box to a set number of previous bounding boxes, each of the set number of previous bounding boxes being from respective, previous image data captured by the at least one camera sensor; and determine a confidence level for the bounding box based on the comparison.

Example 13. The system of example 12, wherein the processing circuitry is further configured to: determine that the confidence level is relatively low; and based on the confidence level being relatively low, at least one of discard the bounding box, down weight values of pixels within the bounding box captured by the at least one camera sensor in a current frame, or output the confidence level.

Example 14. A method of non-contact monitoring respiration of a patient, the method comprising: obtaining image data from at least one camera sensor; determining a visualization mask based on pixels within the image data associated with respiration; determining, a bounding box for the image data based on the visualization mask; determining a sampling region for the current frame of the image data, the sampling region being based on an average of the bounding box for the image data and at least one previously determined bounding box; determining at least a portion of a volume waveform based at least in part on the sampling region for the current frame of the image data; determining at least one respiration parameter based on the volume waveform; and outputting, for display, the at least one respiration parameter based on the volume waveform.

Example 15. The method of example 14, further comprising: determining a region of interest (ROI) of the image data, the ROI comprising a portion of a field of view of the at least one camera sensor; determining that the bounding box extends beyond the ROI; and based on the bounding box extending beyond the ROI, setting the bounding box to equal the ROI.

Example 16. The method of example 14, further comprising: determining a region of interest (ROI) of the image data, the ROI comprising a portion of a field of view of the at least one camera sensor; determining that the bounding box is less than a threshold size; and based on the bounding box being less than the threshold size, setting the bounding box to be equal to the ROI.

Example 17. The method of example 16, wherein the threshold size is a percentage of the ROI.

Example 18. The method of any of examples 14-17, wherein determining the sampling region comprises determining $box_{sampling}=q*mask_{bbox}+(q-1)*box_{sampling}$, where $box_{sampling}$ is the sampling region, $mask_{bbox}$ is the bounding box, $q<1$, and $box_{previoussampling}$ is a previous sampling region.

Example 19. The method of example 18, wherein q is equal to 0.1.

Example 20. The method of any of examples 14-19, further comprising: determining a region of interest (ROI) of the image data, the ROI comprising a portion of a field of view of the at least one camera sensor; determining that a location of pixels of included in at least one of the visualization mask or the bounding box has moved more than a set distance from the image data to previous image data in less than a set time period; and based on the location of pixels of included in the at least one of the visualization mask or the bounding box moving more than a set distance in less than a set time period, setting the bounding box to equal the ROI.

Example 21. The method of any of examples 14-20, wherein determining the bounding box comprises at least one of: executing a bounding box algorithm to determine the bounding box; determining a visualization mask of pixels associated with respiration based on depth data, wherein the bounding box is a smallest rectangle that includes the visualization mask; or executing a semantic segmentation algorithm to determine the visualization mask, wherein the bounding box is the smallest rectangle that includes the visualization mask.

Example 22. The method of any of examples 14-20, further comprising adding a margin to the bounding box.

Example 23. The method of any of examples 14-22, further comprising: determining a plurality of bounding boxes, the plurality of bounding boxes; and determining the bounding box based on the plurality of bounding boxes.

Example 24. The method of example 23, further comprising setting the bounding box to be equal to an average extent of each of the plurality of bounding boxes, setting the bounding box to be equal to a majority voted bounding box of the plurality of bounding boxes, setting the bounding box to be a largest bounding box of the plurality of bounding boxes, setting the bounding box to be a superset of the plurality of bounding boxes, or employing non-maximum-suppression to determine the bounding box.

Example 25. The method of any of examples 14-24, further comprising: comparing the bounding box to a number of previous bounding boxes, each of the number of previous bounding boxes being from respective, previous image data captured by the at least one camera sensor; and determining a confidence level for the bounding box based on the comparison.

Example 26. The method of example 25, further comprising: determining that the confidence level is relatively low; and based on the confidence level being relatively low, at least one of discarding the bounding box, down weighting values of pixels within the bounding box captured by the at least one depth camera in a current frame, or outputting the confidence level.

Example 27. A non-transitory computer-readable storage medium storing instructions, which when executed, cause processing circuitry to: obtain image data from at least one camera sensor; determine a visualization mask based on pixels within the image data associated with respiration; determine, based on pixels within the image data associated with respiration, a bounding box for the image data; determine a sampling region for the image data, the sampling region being based on an average of the bounding box for the image data and at least one previously determined bounding box; determine at least a portion of a volume waveform based at least in part on the sampling region for the image data; determine at least one respiration parameter based on the volume waveform; and output, for display, the least one respiration parameter based on the volume waveform.

Various aspects of the disclosure have been described. These and other aspects are within the scope of the following claims.

What is claimed is:

1. A system for non-contact monitoring respiration of a patient comprising:

at least one camera sensor having a field of view (FOV) and configured to capture image data associated with a patient;

a memory; and processing circuitry coupled to the at least one camera sensor and the memory, the processing circuitry being configured to:

obtain the image data;

determine a region of interest (ROI) of the image data, the ROI comprising a portion of the FOV of the at least one camera sensor;

determine a bounding box for the image data based on pixels within the image data associated with respiration;

determine that a location of the pixels within the bounding box have moved more than a set distance in less than a set time period as compared to pixels associated with respiration in previously obtained image data;

in response to determining that the location of the pixels within the bounding box have moved more than a set distance in less than a set time period, set the bounding box to equal the ROI;

determine a sampling region, the sampling region being based on an average including the bounding box and at least one previously determined bounding box;

determine at least a portion of a volume waveform based at least in part on the sampling region;

determine at least one respiration parameter based on the volume waveform; and output, for display, the at least one respiration parameter.

2. The system of claim 1, wherein the processing circuitry is further configured to:

prior to determining that the location of the pixels within the bounding box have moved more than a set distance in less than a set time period, determine that the bounding box extends beyond the ROI.

3. The system of claim 1, wherein the processing circuitry is further configured to:

prior to determining that the location of the pixels within the bounding box have moved more than a set distance in less than a set time period, determine that the bounding box is less than a threshold size.

4. The system of claim 1, wherein as part of determining the sampling region, the processing circuitry is configured to determine the average based on the equation $box_{sampling}=q*mask_{bbox}+(q-1)*box_{previoussampling}$, where $box_{sampling}$ is the sampling region, $mask_{bbox}$ is the bounding box, $q<1$, and $box_{previoussampling}$ is a previously determined sampling region.

5. The system of claim 1, wherein as part of determining the sampling region, the processing circuitry is configured to determine a running average based on the bounding box and a set number of immediately preceding previously determined bounding boxes.

6. The system of claim 1, wherein as part of determining the bounding box, the processing circuitry is configured to at least one of:

execute a bounding box algorithm to determine the bounding box;

determine a visualization mask, the visualization mask comprising the pixels within the image data associated with respiration, wherein the bounding box is a smallest rectangle that includes all of the visualization mask; or execute a semantic segmentation algorithm to determine the visualization mask, wherein the bounding box is the smallest rectangle that includes all of the visualization mask.

7. The system of claim 1, wherein the processing circuitry is further configured to:

determine a plurality of bounding boxes, each of the plurality of bounding boxes determined using a different method; and determine the bounding box based on the plurality of bounding boxes.

8. The system of claim 7, wherein as part of determining the bounding box based on the plurality of bounding boxes, the processing circuitry is configured to execute one of:

set the bounding box to be equal to an average extent of each of the plurality of bounding boxes;

set the bounding box to be equal to a majority voted bounding box of the plurality of bounding boxes;

set the bounding box to be equal to a majority voted bounding box of the plurality of bounding boxes that is further adjusted to be a largest or a smallest bounding box of the majority voted bounding box;

set the bounding box to be the largest bounding box of the plurality of bounding boxes:

set the bounding box to be a region of overlap of all of the plurality of bounding boxes;

set the bounding box to be a superset of the plurality of bounding boxes; or employ non-maximum-suppression to determine the bounding box based on the plurality of bounding boxes.

9. A method of non-contact monitoring respiration of a patient, the method comprising:

obtaining image data from at least one camera sensor having a field of view (FOV);

determining a region of interest (ROI) of the image data, the ROI comprising a portion of the FOV of the at least one camera sensor;

determining a visualization mask based on pixels within the image data associated with respiration;

determining a bounding box for the image data based on the visualization mask;

determining that a location of the pixels within at least one of the bounding box or the visualization mask have moved more than a set distance in less than a set time period as compared to pixels associated with respiration in previously obtained image data;

in response to determining that the location of the pixels within at least one of the bounding box or the visualization mask have moved more than a set distance in less than a set time period, setting the bounding box to equal the ROI;

determining a sampling region for the image data, the sampling region being based on an average including the bounding box and at least one previously determined bounding box;

determining at least a portion of a volume waveform based at least in part on the sampling region; and determining at least one respiration parameter based on the volume waveform; and outputting, for display, the at least one respiration parameter.

10. The method of claim 9, wherein determining the sampling region comprises determining the average based on the equation $box_{sampling}=q*mask_{bbox}+(q-1)*box_{previoussampling}$, where $box_{sampling}$ is the sampling region, $mask_{bbox}$ is the bounding box, $q<1$, and $box_{previoussampling}$ is a previously determined sampling region.

11. The system of claim 9, wherein determining the sampling region comprises determining a running average based on the bounding box and a set number of immediately preceding previously determined bounding boxes.

12. The method of any of claim 9, further comprising:

determining a plurality of bounding boxes, each of the plurality of bounding boxes determined using a different method; and determining the bounding box based on the plurality of bounding boxes.

13. The method of claim 12, further comprising executing one of:

setting the bounding box to be equal to an average extent of each of the plurality of bounding boxes;

setting the bounding box to be equal to a majority voted bounding box of the plurality of bounding boxes;

setting the bounding box to be equal to a majority voted bounding box of the plurality of bounding boxes that is further adjusted to be a largest or a smallest bounding box of the majority voted bounding box;

setting the bounding box to be the largest bounding box of the plurality of bounding boxes;

setting the bounding box to be a region of overlap of all of the plurality of bounding boxes;

setting the bounding box to be a superset of the plurality of bounding boxes; or employing non-maximum-suppression to determine the bounding box based on the plurality of bounding boxes.

* * * * *